United States Patent
Amis et al.

(10) Patent No.: US 10,328,308 B2
(45) Date of Patent: *Jun. 25, 2019

(54) VISUALIZATION OF ATHLETIC ACTIVITY

(71) Applicant: NIKE, Inc., Beaverton, OR (US)

(72) Inventors: Sam Amis, Portland, OR (US); Christopher Andon, Portland, OR (US); SantoshKumar Balakrishnan, Hillsboro, OR (US); Jenny Campbell, Beaverton, OR (US)

(73) Assignee: NIKE, Inc., Beaverton, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/798,603

(22) Filed: Oct. 31, 2017

(65) Prior Publication Data
US 2018/0050236 A1 Feb. 22, 2018

Related U.S. Application Data

(63) Continuation of application No. 14/613,146, filed on Feb. 3, 2015, now Pat. No. 9,849,335.

(60) Provisional application No. 61/935,210, filed on Feb. 3, 2014.

(51) Int. Cl.
| | | |
|---|---|---|
| A63B 71/00 | (2006.01) | |
| A63B 24/00 | (2006.01) | |
| A63B 71/06 | (2006.01) | |
| G06F 19/00 | (2018.01) | |
| A61B 5/00 | (2006.01) | |
| A61B 5/11 | (2006.01) | |

(52) U.S. Cl.
CPC ........ *A63B 24/0062* (2013.01); *A61B 5/0022* (2013.01); *A61B 5/0024* (2013.01); *A61B 5/1118* (2013.01); *A61B 5/681* (2013.01); *A61B 5/6807* (2013.01); *A63B 71/06* (2013.01); *A63B 71/0622* (2013.01); *G06F 19/00* (2013.01); *G06F 19/34* (2013.01); *A61B 2503/10* (2013.01)

(58) Field of Classification Search
CPC ..... A61B 5/1118; A61B 5/6813; A61B 5/681; A61B 2503/10; A61B 5/0022; A63B 24/0062; A63B 2024/0068; A63B 71/06; A63B 71/0622

See application file for complete search history.

(56) References Cited

U.S. PATENT DOCUMENTS

| | | | |
|---|---|---|---|
| 2006/0064325 A1 | 3/2006 | Matsumoto et al. | |
| 2007/0033069 A1* | 2/2007 | Rao | A63B 24/00 705/2 |
| 2007/0271065 A1 | 11/2007 | Gupta et al. | |
| 2009/0131089 A1* | 5/2009 | Micali | H04L 67/306 455/466 |
| 2009/0190189 A1 | 7/2009 | Suga | |

(Continued)

FOREIGN PATENT DOCUMENTS

EP 2253355 A2 11/2010

OTHER PUBLICATIONS

Apr. 30, 2015—(WO) ISR—App. No. PCT/US2015014293.

*Primary Examiner* — Justin L Myhr
(74) *Attorney, Agent, or Firm* — Banner & Witcoff, Ltd.

(57) ABSTRACT

Example embodiments relate to systems, methods, apparatuses, and computer readable media relating to a user interface, that may for example, receive and/or process physical activity data and allow interaction with the received information in novel implementations.

27 Claims, 20 Drawing Sheets

(56) References Cited

U.S. PATENT DOCUMENTS

| | | |
|---|---|---|
| 2010/0185398 A1 | 7/2010 | Bems et al. |
| 2010/0292050 A1 | 11/2010 | DiBenedetto et al. |
| 2012/0015778 A1 | 1/2012 | Lee et al. |
| 2012/0198347 A1* | 8/2012 | Hirvonen .......... G06F 17/30867 |
| | | 715/738 |
| 2015/0213257 A1 | 7/2015 | Lai et al. |

* cited by examiner

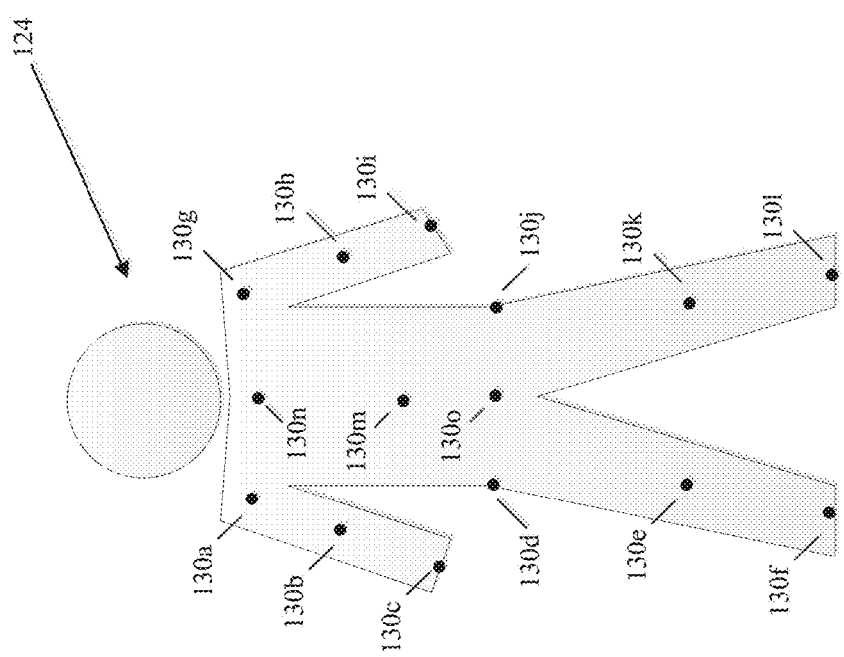

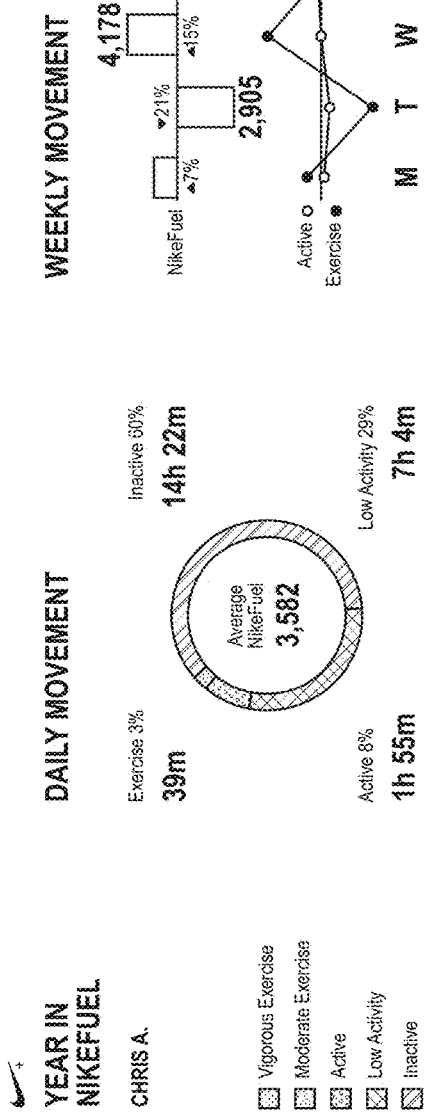
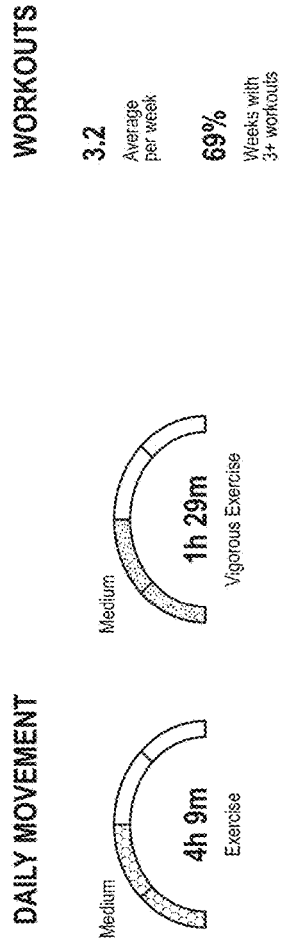

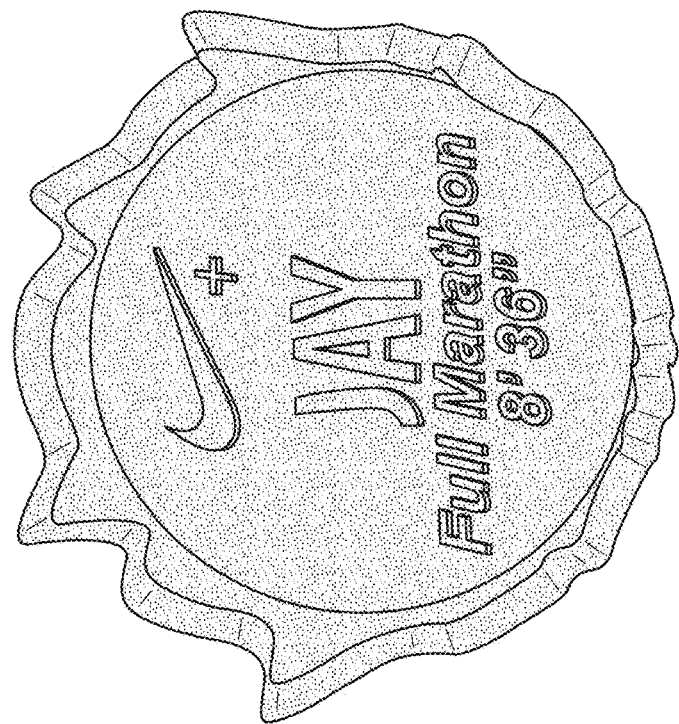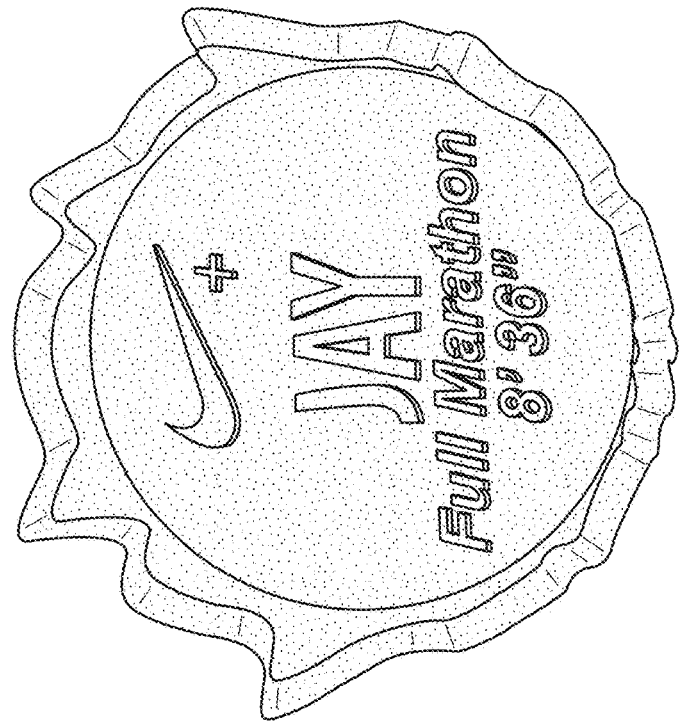
FIG. 15

VISUALIZATION OF ATHLETIC ACTIVITY

CROSS-REFERENCE TO RELATED APPLICATIONS

The present application claims the benefit of and is a continuation of U.S. patent application Ser. No. 14/613,146 filed Feb. 3, 2015, which claims the benefit of and priority to U.S. Provisional Patent Application No. 61/935,210, entitled "VISUALIZATION OF ATHLETIC ACTIVITY" and filed Feb. 3, 2014, the entire disclosures of which are hereby incorporated by reference in their entirety.

BACKGROUND

While most people appreciate the importance of physical fitness, many have difficulty finding the motivation required to maintain a regular exercise program. Some people find it particularly difficult to maintain an exercise regimen that involves continuously repetitive motions, such as running, walking and bicycling.

Additionally, individuals may view exercise as work or a chore and thus, separate it from enjoyable aspects of their daily lives. Often, this clear separation between athletic activity and other activities reduces the amount of motivation that an individual might have toward exercising. Further, athletic activity services and systems directed toward encouraging individuals to engage in athletic activities might also be too focused on one or more particular activities while an individual's interest are ignored. This may further decrease a user's interest in participating in athletic activities or using the athletic activity services and systems.

Therefore, improved systems and methods to address these and other shortcomings in the art are desired.

BRIEF SUMMARY

The following presents a simplified summary in order to provide a basic understanding of some aspects of the disclosure. The summary is not an extensive overview of the disclosure. It is neither intended to identify key or critical elements of the disclosure nor to delineate the scope of the disclosure. The following summary merely presents some concepts of the disclosure in a simplified form as a prelude to the description below.

One or more aspects describe systems, apparatuses, computer readable media, and methods for tracking performance metrics of a user during an exercise session.

Aspects of this disclosure relate to calculating energy expenditure values. In certain embodiments, energy expenditure points may be calculated. One or more devices may use an accelerometer and/or other sensors to monitor activity of a user. Under certain implementations, a user may earn energy expenditure points for different activities.

One or more aspects describe systems and methods for tracking athletic activity metrics of one or more users over time. Metrics may be recorded continuously or based on a predefined schedule. In either case, multiple values may be recorded for the one or more tracked activity metrics and associated with the particular time period or specific time at which the values were detected. For examples, athletic performance data may be detected and recorded for every minimum time unit. The minimum time unit may correspond to 1 second, 2 seconds, a millisecond, 10 seconds and the like. Using such time-based recordings, the user may review instantaneous and specific metric values to determine how they were performing at particular points during an athletic activity performance, or over a plurality of athletic activity performances.

According to another aspect, users may display the multiple metrics simultaneously in an interface during review of the athletic activity session. For example, a user may display a visualization of athletic activity performed by the user over time in conjunction with graphic overlays of one or more desired metrics. Additionally or alternatively, a toolbar may be displayed to provide other metrics not currently displayed in the visualization interface display.

According to other aspects of the present disclosure, users may generate unique activity designs based on athletic activity data collected for the user over a period of time. The unique activity design for a user may represent a visual or digital athletic signature (e.g., fingerprint, watermark) to identify the user. In some aspects of the present disclosure, activity design data may be utilized for the purpose of confirming or validating a user's identity.

In some embodiments, the present invention can be partially or wholly implemented on a computer-readable medium, for example, by storing computer-executable instructions or modules, or by utilizing computer-readable data structures.

Of course, the methods and systems of the above-referenced embodiments may also include other additional elements, steps, computer-executable instructions, or computer-readable data structures.

The details of these and other embodiments of the present invention are set forth in the accompanying drawings and the description below. Other features and advantages of the invention will be apparent from the description and drawings, and from the claims.

BRIEF DESCRIPTION OF THE DRAWINGS

FIG. 5 shows illustrative locations for sensory input which may include physical sensors located on/in a user's clothing and/or be based upon identification of relationships between two moving body parts of the user;

FIGS. 9C-F show an example display of sub-interfaces for an activity data interface in accordance with example embodiments;

FIG. 15 shows an illustration of an example activity reward in accordance with example embodiments;

DETAILED DESCRIPTION

Aspects of this disclosure involve obtaining, storing, and/or processing athletic data relating to the physical movements of an athlete. The athletic data may be actively or passively sensed and/or stored in one or more non-transitory storage mediums. Still further aspects relate to using athletic data to generate an output, such as for example, calculated athletic attributes, feedback signals to provide guidance, and/or other information. These and other aspects will be discussed in the context of the following illustrative examples of a personal training system.

In the following description of the various embodiments, reference is made to the accompanying drawings, which form a part hereof, and in which is shown by way of illustration various embodiments in which aspects of the disclosure may be practiced. It is to be understood that other embodiments may be utilized and structural and functional modifications may be made without departing from the scope and spirit of the present disclosure. Further, headings within this disclosure should not be considered as limiting aspects of the disclosure and the example embodiments are not limited to the example headings.

I. Example Personal Training System

A. Illustrative Networks

Figure 1:
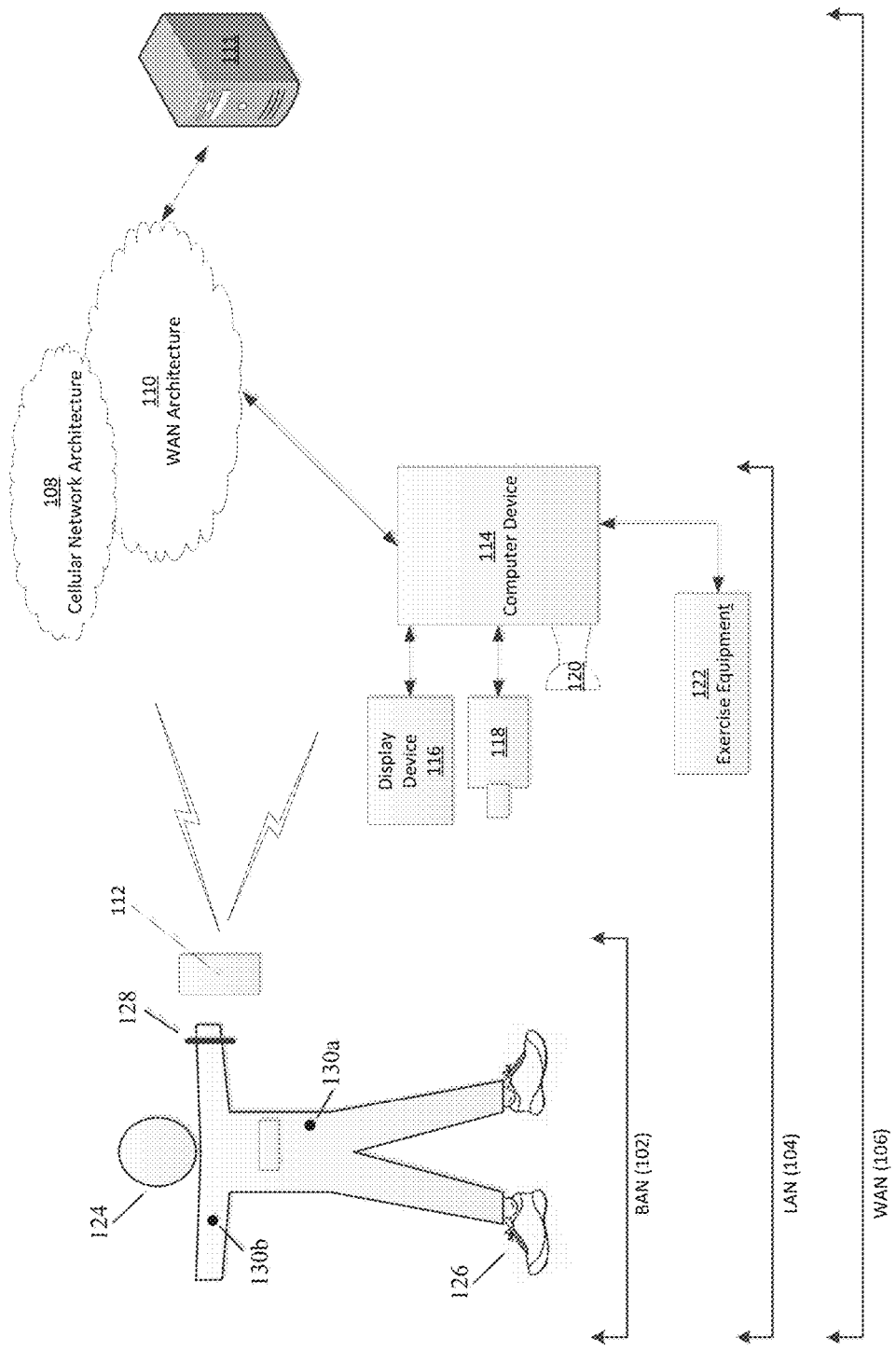
FIG. 1 illustrates an example system that may be configured to provide personal training and/or obtain data from the physical movements of a user in accordance with example embodiments.

Aspects of this disclosure relate to systems and methods that may be utilized across a plurality of networks. In this regard, certain embodiments may be configured to adapt to dynamic network environments. Further embodiments may be operable in differing discrete network environments. FIG. 1 illustrates an example of a personal training system 100 in accordance with example embodiments. Example system 100 may include one or more interconnected networks, such as the illustrative body area network (BAN) 102, local area network (LAN) 104, and wide area network (WAN) 106. As shown in FIG. 1 (and described throughout this disclosure), one or more networks (e.g., BAN 102, LAN 104, and/or WAN 106), may overlap or otherwise be inclusive of each other. Those skilled in the art will appreciate that the illustrative networks 102-106 are logical networks that may each comprise one or more different communication protocols and/or network architectures and yet may be configured to have gateways to each other or other networks. For example, each of BAN 102, LAN 104 and/or WAN 106 may be operatively connected to the same physical network architecture, such as cellular network architecture 108 and/or WAN architecture 110. For example, portable electronic device 112, which may be considered a component of both BAN 102 and LAN 104, may comprise a network adapter or network interface card (NIC) configured to translate data and control signals into and from network messages according to one or more communication protocols, such as the Transmission Control Protocol (TCP), the Internet Protocol (IP), and the User Datagram Protocol (UDP) through one or more of architectures 108 and/or 110. These protocols are well known in the art, and thus will not be discussed here in more detail.

Network architectures 108 and 110 may include one or more information distribution network(s), of any type(s) or topology(s), alone or in combination(s), such as for example, cable, fiber, satellite, telephone, cellular, wireless, etc. and as such, may be variously configured such as having one or more wired or wireless communication channels (including but not limited to: WiFi®, Bluetooth®, Near-Field Communication (NFC) and/or ANT technologies). Thus, any device within a network of FIG. 1, (such as portable electronic device 112 or any other device described herein) may be considered inclusive to one or more of the different logical networks 102-106. With the foregoing in mind, example components of an illustrative BAN and LAN (which may be coupled to WAN 106) will be described.

1. Example Local Area Network

LAN 104 may include one or more electronic devices, such as for example, computer device 114. Computer device 114, or any other component of system 100, may comprise a mobile terminal, such as a telephone, music player, tablet, netbook or any portable device. In other embodiments, computer device 114 may comprise a media player or recorder, desktop computer, server(s), a gaming console, such as for example, a Microsoft® XBOX, Sony® Playstation, and/or a Nintendo® Wii gaming consoles. Those skilled in the art will appreciate that these are merely example devices for descriptive purposes and this disclosure is not limited to any console or computing device.

Figure 2:
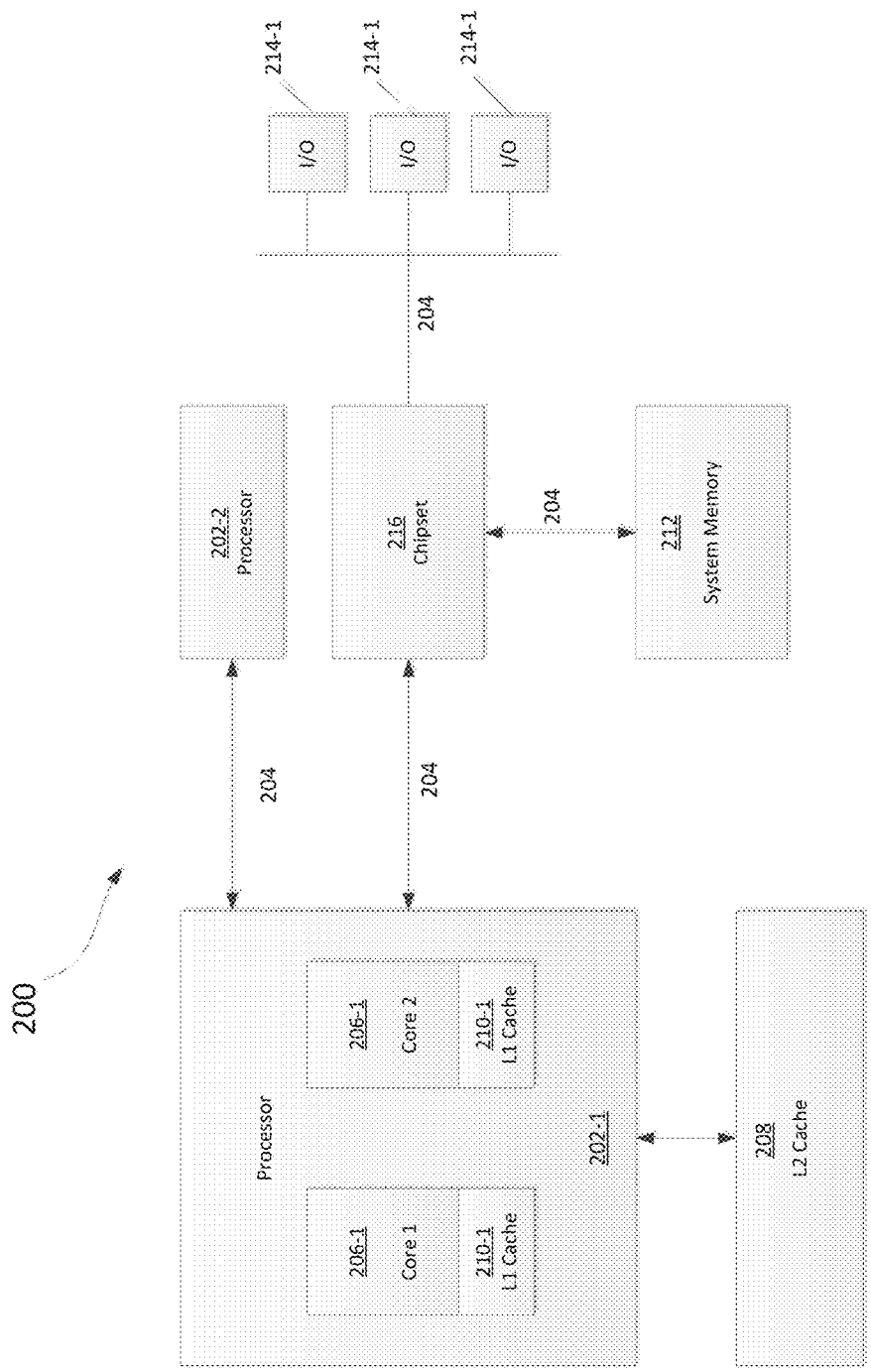
FIG. 2 illustrates an example computer device that may be part of or in communication with the system of FIG. 1.

Those skilled in the art will appreciate that the design and structure of computer device 114 may vary depending on several factors, such as its intended purpose. One example implementation of computer device 114 is provided in FIG. 2, which illustrates a block diagram of computing device 200. Those skilled in the art will appreciate that the disclosure of FIG. 2 may be applicable to any device disclosed herein. Device 200 may include one or more processors, such as processor 202-1 and 202-2 (generally referred to herein as "processors 202" or "processor 202"). Processors 202 may communicate with each other or other components via an interconnection network or bus 204. Processor 202 may include one or more processing cores, such as cores 206-1 and 206-2 (referred to herein as "cores 206" or more generally as "core 206"), which may be implemented on a single integrated circuit (IC) chip.

Cores 206 may comprise a shared cache 208 and/or a private cache (e.g., caches 210-1 and 210-2, respectively). One or more caches 208/210 may locally cache data stored in a system memory, such as memory 212, for faster access by components of the processor 202. Memory 212 may be in communication with the processors 202 via a chipset 216. Cache 208 may be part of system memory 212 in certain embodiments. Memory 212 may include, but is not limited to, random access memory (RAM), read only memory (ROM), and include one or more of solid-state memory, optical or magnetic storage, and/or any other medium that can be used to store electronic information. Yet other embodiments may omit system memory 212.

System 200 may include one or more I/O devices (e.g., I/O devices 214-1 through 214-3, each generally referred to as I/O device 214). I/O data from one or more I/O devices 214 may be stored at one or more caches 208, 210 and/or system memory 212. Each of I/O devices 214 may be permanently or temporarily configured to be in operative communication with a component of system 100 using any physical or wireless communication protocol.

Returning to FIG. 1, four example I/O devices (shown as elements 116-122) are shown as being in communication with computer device 114. Those skilled in the art will appreciate that one or more of devices 116-122 may be stand-alone devices or may be associated with another device besides computer device 114. For example, one or more I/O devices may be associated with or interact with a component of BAN 102 and/or WAN 106. I/O devices 116-122 may include, but are not limited to athletic data acquisition units, such as for example, sensors. One or more I/O devices may be configured to sense, detect, and/or measure an athletic parameter from a user, such as user 124. Examples include, but are not limited to: an accelerometer, a gyroscope, a location-determining device (e.g., GPS), light (including non-visible light) sensor, temperature sensor (including ambient temperature and/or body temperature), sleep pattern sensors, heart rate monitor, image-capturing sensor, moisture sensor, force sensor, compass, angular rate sensor, and/or combinations thereof among others.

In further embodiments, I/O devices 116-122 may be used to provide an output (e.g., audible, visual, or tactile cue) and/or receive an input, such as a user input from athlete 124. Example uses for these illustrative I/O devices are provided below, however, those skilled in the art will appreciate that such discussions are merely descriptive of some of the many options within the scope of this disclosure. Further, reference to any data acquisition unit, I/O device, or sensor is to be interpreted disclosing an embodiment that may have one or more I/O device, data acquisition unit, and/or sensor disclosed herein or known in the art (either individually or in combination).

Information from one or more devices (across one or more networks) may be used to provide (or be utilized in the formation of) a variety of different parameters, metrics or physiological characteristics including but not limited to: motion parameters, such as speed, acceleration, distance, steps taken, direction, relative movement of certain body portions or objects to others, or other motion parameters which may be expressed as angular rates, rectilinear rates or combinations thereof, physiological parameters, such as calories, heart rate, sweat detection, effort, oxygen consumed, oxygen kinetics, and other metrics which may fall within one or more categories, such as: pressure, impact forces, information regarding the athlete, such as height, weight, age, demographic information and combinations thereof.

System 100 may be configured to transmit and/or receive athletic data, including the parameters, metrics, or physiological characteristics collected within system 100 or otherwise provided to system 100. As one example, WAN 106 may comprise server 111. Server 111 may have one or more components of system 200 of FIG. 2. In one embodiment, server 111 comprises at least a processor and a memory, such as processor 206 and memory 212. Server 111 may be configured to store computer-executable instructions on a non-transitory computer-readable medium. The instructions may comprise athletic data, such as raw or processed data collected within system 100. System 100 may be configured to transmit data, such as energy expenditure points, to a social networking website or host such a site. Server 111 may be utilized to permit one or more users to access and/or compare athletic data. As such, server 111 may be configured to transmit and/or receive notifications based upon athletic data or other information.

Returning to LAN 104, computer device 114 is shown in operative communication with a display device 116, an image-capturing device 118, sensor 120 and exercise device 122, which are discussed in turn below with reference to example embodiments. In one embodiment, display device 116 may provide audio-visual cues to athlete 124 to perform a specific athletic movement. The audio-visual cues may be provided in response to computer-executable instruction executed on computer device 114 or any other device, including a device of BAN 102 and/or WAN. Display device 116 may be a touchscreen device or otherwise configured to receive a user-input.

In one embodiment, data may be obtained from image-capturing device 118 and/or other sensors, such as sensor 120, which may be used to detect (and/or measure) athletic parameters, either alone or in combination with other devices, or stored information. Image-capturing device 118 and/or sensor 120 may comprise a transceiver device. In one embodiment sensor 128 may comprise an infrared (IR), electromagnetic (EM) or acoustic transceiver. For example, image-capturing device 118, and/or sensor 120 may transmit waveforms into the environment, including towards the direction of athlete 124 and receive a "reflection" or otherwise detect alterations of those released waveforms. Those skilled in the art will readily appreciate that signals corresponding to a multitude of different data spectrums may be utilized in accordance with various embodiments. In this regard, devices 118 and/or 120 may detect waveforms emitted from external sources (e.g., not system 100). For example, devices 118 and/or 120 may detect heat being emitted from user 124 and/or the surrounding environment. Thus, image-capturing device 126 and/or sensor 128 may comprise one or more thermal imaging devices. In one embodiment, image-capturing device 126 and/or sensor 128 may comprise an IR device configured to perform range phenomenology.

In some aspects of the present disclosure, sensor 128 may comprise a plurality of different sensors. In an example embodiment, the sensor may comprise or permit operative connection to an accelerometer (including in the form of a multi-axis accelerometer), heart rate sensor, location-determining sensor, such as a GPS sensor, and/or other sensors. Detected movements or parameters from device's 128 sensor(s), may include (or be used to form) a variety of different parameters, metrics or physiological characteristics including but not limited to speed, distance, steps taken, calories, heart rate, sweat detection, effort, oxygen consumed, and/or oxygen kinetics. Such parameters may also be expressed in terms of activity points or currency earned by the user based on the activity of the user. Activity points may represent a statistic indicating physical activity performed by a user. Additionally or alternatively, activity points may be awarded to the user upon achieving certain athletic milestones. The number of activity points earned by a user may within a particular time period may be assigned a specified value (e.g. activity point value).

In one embodiment, exercise device 122 may be any device configurable to permit or facilitate the athlete 124 performing a physical movement, such as for example a treadmill, step machine, etc. There is no requirement that the device be stationary. In this regard, wireless technologies permit portable devices to be utilized, thus a bicycle or other mobile exercising device may be utilized in accordance with certain embodiments. Those skilled in the art will appreciate that equipment 122 may be or comprise an interface for receiving an electronic device containing athletic data performed remotely from computer device 114. For example, a user may use a sporting device (described below in relation to BAN 102) and upon returning home or the location of equipment 122, download athletic data into element 122 or any other device of system 100. Any I/O device disclosed herein may be configured to receive activity data.

2. Body Area Network

BAN 102 may include two or more devices configured to receive, transmit, or otherwise facilitate the collection of athletic data (including passive devices). Exemplary devices may include one or more data acquisition units, sensors, or devices known in the art or disclosed herein, including but not limited to I/O devices 116-122. Two or more components of BAN 102 may communicate directly, yet in other embodiments, communication may be conducted via a third device, which may be part of BAN 102, LAN 104, and/or WAN 106. One or more components of LAN 104 or WAN 106 may form part of BAN 102. In certain implementations, whether a device, such as portable device 112, is part of BAN 102, LAN 104, and/or WAN 106, may depend on the athlete's proximity to an access point to permit communication with mobile cellular network architecture 108 and/or WAN architecture 110. User activity and/or preference may also influence whether one or more components are utilized as part of BAN 102. Example embodiments are provided below.

User 124 may be associated with (e.g., possess, carry, wear, and/or interact with) any number of devices, such as portable device 112, shoe-mounted device 126, wrist-worn device 128 and/or a sensing location, such as sensing location 130, which may comprise a physical device or a location that is used to collect information. One or more devices 112, 126, 128, and/or 130 may not be specially designed for fitness or athletic purposes. Indeed, aspects of this disclosure relate to utilizing data from a plurality of devices, some of which are not fitness devices, to collect, detect, and/or measure athletic data. In certain embodiments, one or more devices of BAN 102 (or any other network) may comprise a fitness or sporting device that is specifically designed for a particular sporting use. As used herein, the term "sporting device" includes any physical object that may be used or implicated during a specific sport or fitness activity. Exemplary sporting devices may include, but are not limited to: golf balls, basketballs, baseballs, soccer balls, footballs, powerballs, hockey pucks, weights, bats, clubs, sticks, paddles, mats, and combinations thereof. In further embodiments, exemplary fitness devices may include objects within a sporting environment where a specific sport occurs, including the environment itself, such as a goal net, hoop, backboard, portions of a field, such as a midline, outer boundary marker, base, and combinations thereof.

In this regard, those skilled in the art will appreciate that one or more sporting devices may also be part of (or form) a structure and vice-versa, a structure may comprise one or more sporting devices or be configured to interact with a sporting device. For example, a first structure may comprise a basketball hoop and a backboard, which may be removable and replaced with a goal post. In this regard, one or more sporting devices may comprise one or more sensors, such as one or more of the sensors discussed above in relation to FIGS. 1-3, that may provide information utilized, either independently or in conjunction with other sensors, such as one or more sensors associated with one or more structures. For example, a backboard may comprise a first sensor configured to measure a force and a direction of the force by a basketball upon the backboard and the hoop may comprise a second sensor to detect a force. Similarly, a golf club may comprise a first sensor configured to detect grip attributes on the shaft and a second sensor configured to measure impact with a golf ball.

Looking to the illustrative portable device 112, it may be a multi-purpose electronic device, that for example, includes a telephone or digital music player, including an IPOD®, IPAD®, or iPhone®, brand devices available from Apple, Inc. of Cupertino, Calif. or Zune® or Microsoft® Windows devices available from Microsoft of Redmond, Wash. As known in the art, digital media players can serve as an output device, input device, and/or storage device for a computer. Device 112 may be configured as an input device for receiving raw or processed data collected from one or more devices in BAN 102, LAN 104, or WAN 106. In one or more embodiments, portable device 112 may comprise one or more components of computer device 114. For example, portable device 112 may be include a display 116, image-capturing device 118, and/or one or more data acquisition devices, such as any of the I/O devices 116-122 discussed above, with or without additional components, so as to comprise a mobile terminal.

a. Illustrative Apparel/Accessory Sensors

In certain embodiments, I/O devices may be formed within or otherwise associated with user's 124 clothing or accessories, including a watch, armband, wristband, necklace, shirt, shoe, or the like. These devices may be configured to monitor athletic movements of a user. It is to be understood that they may detect athletic movement during user's 124 interactions with computer device 114 and/or operate independently of computer device 114 (or any other device disclosed herein). For example, one or more devices in BAN 102 may be configured to function as an all-day activity monitor that measures activity regardless of the user's proximity or interactions with computer device 114. It is to be further understood that the sensory system 302 shown in FIG. 3 and the device assembly 400 shown in FIG. 4, each of which are described in the following paragraphs, are merely illustrative examples.

i. Shoe-mounted Device

Figure 3:
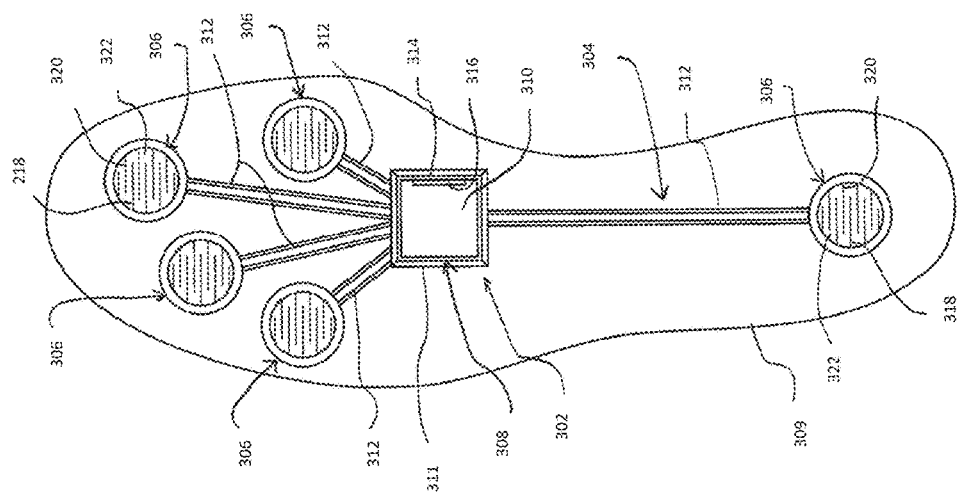
FIG. 3 shows an illustrative sensor assembly that may be worn by a user in accordance with example embodiments.

In certain embodiments, device 126 shown in FIG. 1, may comprise footwear which may include one or more sensors, including but not limited to those disclosed herein and/or known in the art. FIG. 3 illustrates one example embodiment of a sensor system 302 providing one or more sensor assemblies 304. Assembly 304 may comprise one or more sensors, such as for example, an accelerometer, gyroscope, location-determining components, force sensors and/or or any other sensor disclosed herein or known in the art. In the illustrated embodiment, assembly 304 incorporates a plurality of sensors, which may include force-sensitive resistor (FSR) sensors 306; however, other sensor(s) may be utilized. Port 308 may be positioned within a sole structure 309 of a shoe, and is generally configured for communication with one or more electronic devices. Port 308 may optionally be provided to be in communication with an electronic module 310, and the sole structure 309 may optionally include a housing 311 or other structure to receive the module 310. The sensor system 302 may also include a plurality of leads 312 connecting the FSR sensors 306 to the port 308, to enable communication with the module 310 and/or another electronic device through the port 308. Module 310 may be contained within a well or cavity in a sole structure of a shoe, and the housing 311 may be positioned within the well or cavity. In one embodiment, at least one gyroscope and at least one accelerometer are provided within a single housing, such as module 310 and/or housing 311. In at least a further embodiment, one or more sensors are provided that, when operational, are configured to provide directional information and angular rate data. The port 308 and the module 310 include complementary interfaces 314, 316 for connection and communication.

In certain embodiments, at least one force-sensitive resistor 306 shown in FIG. 3 may contain first and second electrodes or electrical contacts 318, 320 and a force-sensitive resistive material 322 disposed between the electrodes 318, 320 to electrically connect the electrodes 318, 320 together. When pressure is applied to the force-sensitive material 322, the resistivity and/or conductivity of the force-sensitive material 322 changes, which changes the electrical potential between the electrodes 318, 320. The change in resistance can be detected by the sensor system 302 to detect the force applied on the sensor 316. The force-sensitive resistive material 322 may change its resistance under pressure in a variety of ways. For example, the force-sensitive material 322 may have an internal resistance that decreases when the material is compressed. Further embodiments may utilize "volume-based resistance", which may be implemented through "smart materials." As another example, the material 322 may change the resistance by changing the degree of surface-to-surface contact, such as between two pieces of the force sensitive material 322 or between the force sensitive material 322 and one or both electrodes 318, 320. In some circumstances, this type of force-sensitive resistive behavior may be described as "contact-based resistance."

ii. Wrist-worn Device

Figure 4:
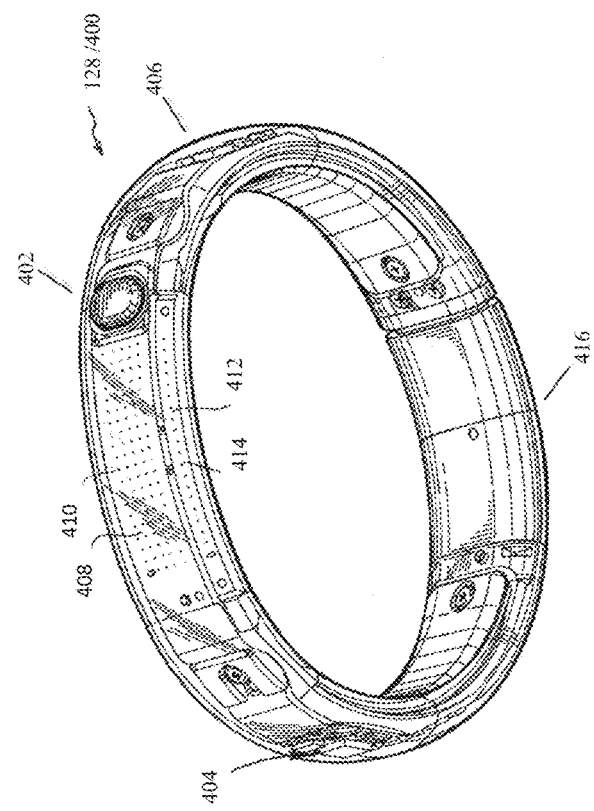
FIG. 4 shows another example sensor assembly that may be worn by a user in accordance with example embodiments.

As shown in FIG. 4, device 400 (which may resemble or comprise sensory device 128 shown in FIG. 1), may be configured to be worn by user 124, such as around a wrist, arm, ankle, neck or the like. Device 400 may include an input mechanism, such as a depressible input button 402 configured to be used during operation of the device 400. The input button 402 may be operably connected to a controller 404 and/or any other electronic components, such as one or more of the elements discussed in relation to computer device 114 shown in FIG. 1. Controller 404 may be embedded or otherwise part of housing 406. Housing 406 may be formed of one or more materials, including elastomeric components and comprise one or more displays, such as display 408. The display may be considered an illuminable portion of the device 400. The display 408 may include a series of individual lighting elements or light members such as LED lights 410. The lights may be formed in an array and operably connected to the controller 404. Device 400 may include an indicator system 412, which may also be considered a portion or component of the overall display 408. Indicator system 412 can operate and illuminate in conjunction with the display 408 (which may have pixel member 414) or completely separate from the display 408. The indicator system 412 may also include a plurality of additional lighting elements or light members, which may also take the form of LED lights in an exemplary embodiment. In certain embodiments, indicator system may provide a visual indication of goals, such as by illuminating a portion of lighting members of indicator system 412 to represent accomplishment towards one or more goals. Device 400 may be configured to display data expressed in terms of activity points or currency earned by the user based on the activity of the user, either through display 408 and/or indicator system 412.

A fastening mechanism 416 can be disengaged wherein the device 400 can be positioned around a wrist or portion of the user 124 and the fastening mechanism 416 can be subsequently placed in an engaged position. In one embodiment, fastening mechanism 416 may comprise an interface, including but not limited to a USB port, for operative interaction with computer device 114 and/or devices, such as devices 120 and/or 112. In certain embodiments, fastening member may comprise one or more magnets. In one embodiment, fastening member may be devoid of moving parts and rely entirely on magnetic forces.

In certain embodiments, device 400 may comprise a sensor assembly (not shown in FIG. 4). The sensor assembly may comprise a plurality of different sensors, including those disclosed herein and/or known in the art. In an example embodiment, the sensor assembly may comprise or permit operative connection to any sensor disclosed herein or known in the art. Device 400 and or its sensor assembly may be configured to receive data obtained from one or more external sensors.

iii. Apparel and/or Body Location Sensing

Element 130 of FIG. 1 shows an example sensory location which may be associated with a physical apparatus, such as a sensor, data acquisition unit, or other device. Yet in other embodiments, it may be a specific location of a body portion or region that is monitored, such as via an image capturing device (e.g., image capturing device 118). In certain embodiments, element 130 may comprise a sensor, such that elements 130*a* and 130*b* may be sensors integrated into apparel, such as athletic clothing. Such sensors may be placed at any desired location of the body of user 124. Sensors 130*a/b* may communicate (e.g., wirelessly) with one or more devices (including other sensors) of BAN 102, LAN 104, and/or WAN 106. In certain embodiments, passive sensing surfaces may reflect waveforms, such as infrared light, emitted by image-capturing device 118 and/or sensor 120. In one embodiment, passive sensors located on user's 124 apparel may comprise generally spherical structures made of glass or other transparent or translucent surfaces which may reflect waveforms. Different classes of apparel may be utilized in which a given class of apparel has specific sensors configured to be located proximate to a specific portion of the user's 124 body when properly worn. For example, golf apparel may include one or more sensors positioned on the apparel in a first configuration and yet soccer apparel may include one or more sensors positioned on apparel in a second configuration.

FIG. 5 shows illustrative locations for sensory input (see, e.g., sensory locations 130*a*-130*o*). In this regard, sensors may be physical sensors located on/in a user's clothing, yet in other embodiments, sensor locations 130*a*-130*o* may be based upon identification of relationships between two moving body parts. For example, sensor location 130*a* may be determined by identifying motions of user 124 with an image-capturing device, such as image-capturing device 118. Thus, in certain embodiments, a sensor may not physically be located at a specific location (such as one or more of sensor locations 130a-130o), but is configured to sense properties of that location, such as with image-capturing device 118 or other sensor data gathered from other locations. In this regard, the overall shape or portion of a user's body may permit identification of certain body parts. Regardless of whether an image-capturing device is utilized and/or a physical sensor located on the user 124, and/or using data from other devices, (such as sensory system 302), device assembly 400 and/or any other device or sensor disclosed herein or known in the art is utilized, the sensors may sense a current location of a body part and/or track movement of the body part. In one embodiment, sensory data relating to location 130m may be utilized in a determination of the user's center of gravity (a.k.a, center of mass).

For example, relationships between location 130a and location(s) 130f/130l with respect to one or more of location(s) 130m-130o may be utilized to determine if a user's center of gravity has been elevated along the vertical axis (such as during a jump) or if a user is attempting to "fake" a jump by bending and flexing their knees. In one embodiment, sensor location 1306n may be located at about the sternum of user 124. Likewise, sensor location 130o may be located approximate to the naval of user 124. In certain embodiments, data from sensor locations 130m-130o may be utilized (alone or in combination with other data) to determine the center of gravity for user 124. In further embodiments, relationships between multiple sensor locations, such as sensors 130m-130o, may be utilized in determining orientation of the user 124 and/or rotational forces, such as twisting of user's 124 torso. Further, one or more locations, such as location(s), may be utilized as (or approximate) a center of moment location. For example, in one embodiment, one or more of location(s) 130m-130o may serve as a point for a center of moment location of user 124. In another embodiment, one or more locations may serve as a center of moment of specific body parts or regions.

II. Athletic Collection and Display Tools

Figure 6A:
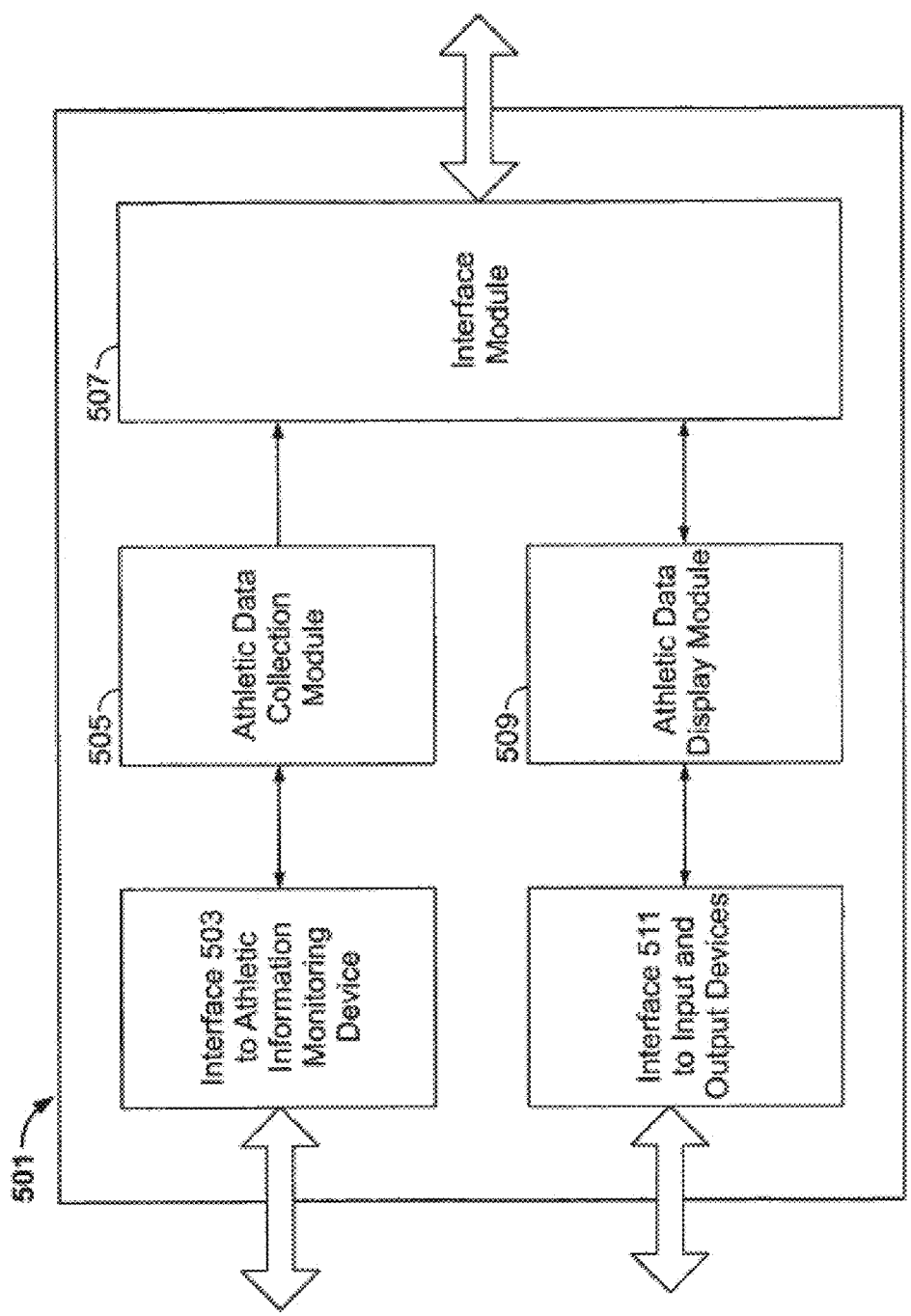
FIG. 6A illustrates an example of an athletic information collection and display device that may be employed to collect and/or display athletic data according to various implementations of the invention.

FIG. 6A illustrates an example of an athletic information collection and display device 501 that may be employed to collect and/or display athletic data according to various implementations of the invention. As will be discussed in more detail below, the athletic information collection and display device 501 may both collect and display athletic data. The athletic information collection and display device 501 may be implemented using any suitable variation of the computing device 101 previously described. In some situations, however, the information collection and display device 501 may be implemented using a desktop, laptop, personal computer, mobile computing device, and the like.

As shown FIG. 6A, the athletic information collection and display device 501 includes an interface 503 for receiving data from device 400. The interface 503 may be implemented using, e.g., electrical components, software components (such as application program interfaces (APIs)), or some combination thereof. The athletic information collection and display device 501 also has an athletic data collection module 505. With various examples of the invention, the athletic data collection module 505 may detect when device 400 or other portable electronic device storing one or more athletic data sets is connected, wirelessly or otherwise, to the athletic information collection and display device 501 through the interface 503, establish a communication session with the device 400 or other portable electronic device to retrieve the athletic data set or sets. In some implementations of the invention, the athletic data collection module 505 may delete athletic data sets from the device 400 or other portable electronic device after the athletic data sets have been retrieved.

With some examples of the invention, the athletic data collection module 505 may perform some further operations on the athletic data sets retrieved from the device 400 or other portable electronic device. For example, if the device 400 can be employed to collect athletic information from different users, then the athletic data collection module 505 may additionally prompt the user to identify himself or herself (if this information was not previously obtained by the athletic information collection and display device 501). This identification information may then be included with the retrieved athletic data sets.

As previously noted, the athletic information collection and display device 501 typically will generate sets of athletic data from information measured by one or more athletic parameter measurement devices, such as device 400. With some embodiments of the invention, however, the athletic information collection and display device 501 may instead store the raw information provided by the device 400. With these embodiments, the athletic data collection module 505 may retrieve the raw information from the device 400 or other portable electronic device, and then generate athletic data sets from the raw information itself.

The athletic data collection module 505 may be implemented by, for example, software instructions executed by a computing device, such as computer device 114. With some examples of the invention the athletic data collection module 505 may be implemented by a conventional software tool, such as a browser. Alternately, athletic data collection module 505 may be implemented by a purpose-specific software tool or by a conventional software tool enhanced to perform athletic data collection functions. For example, the athletic data collection module 505 may be implemented by a software tool that incorporates a conventional browser to perform a variety of functions.

Once the athletic data collection module 505 has collected the processed signals provided by an athletic information monitoring device, such as device 400, the athletic data collection module 505 transmits the athletic data set to an athletic data display configuration device 601 through an interface module 507. The athletic information collection and display device 501 may communicate with the athletic data display configuration device 601 through a conventional network, such as the Internet. With these configurations, the interface module 507 may be implemented using any conventional type of network interface, such as a network interface card. Of course, any type of desired hardware or software combination alternately may be used to allow the athletic data collection module 505 to send the collected athletic data to the athletic data display configuration device 601. With some implementations of the invention, the athletic data collection module 505 may automatically forward collected athletic data to the athletic data display configuration device 601. For example, the athletic data collection module 505 may attempt to forward collected athletic data to the athletic data display configuration device 601 immediately after collection, at a prescheduled interval, upon the detection of a network connection to the athletic data display configuration device 601, or some combination thereof. Alternately or additionally, the athletic data collection module 505 may prompt a user to specify when collected athletic data is sent to the athletic data display configuration device 601.

Figure 6B:
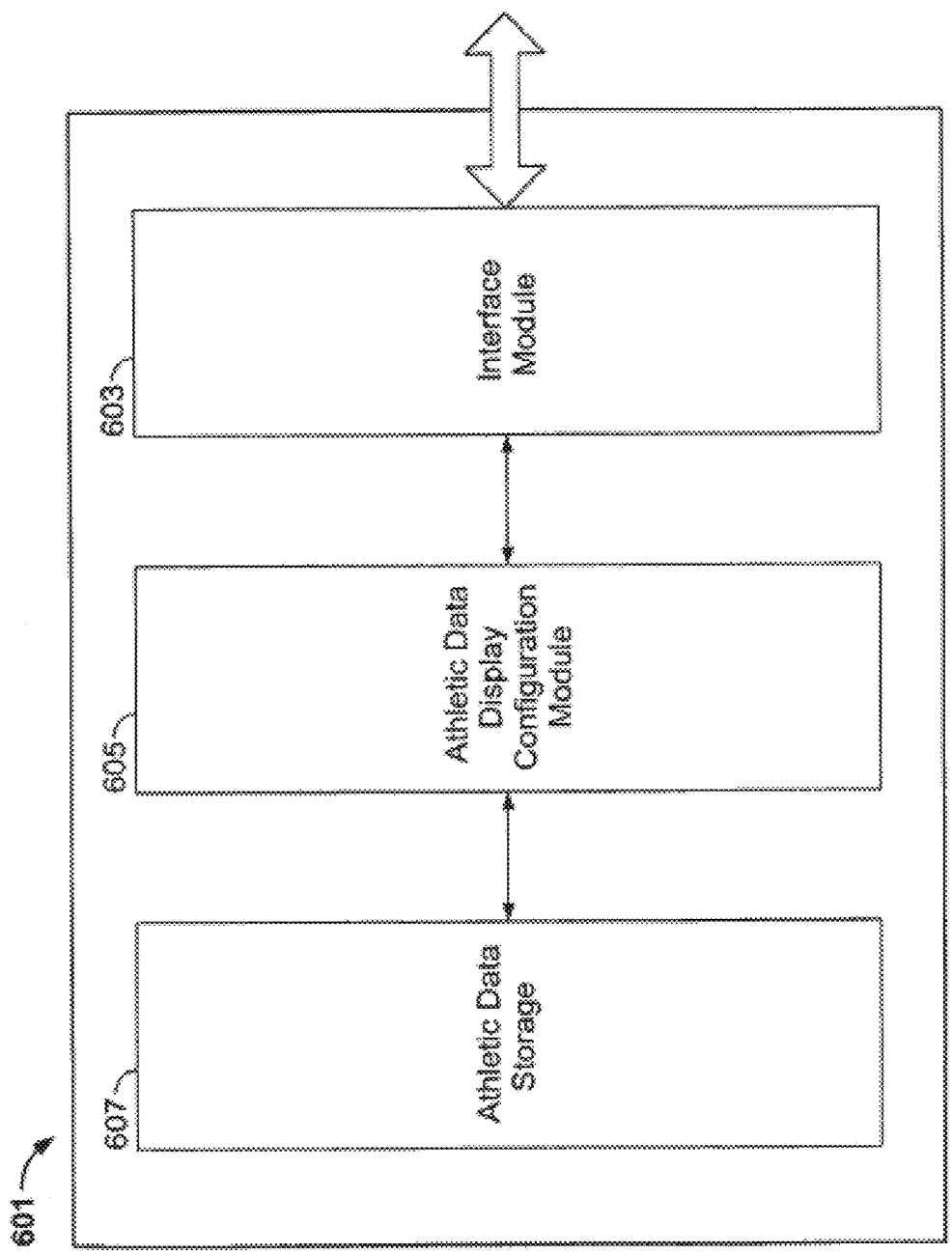
FIG. 6B illustrates an example of an athletic data display configuration device that may be employed according to various examples of the invention.

FIG. 6 illustrates an example of an athletic data display configuration device 601 that may be employed according to various examples of the invention. As seen in this figure, the athletic data display configuration device 601 includes an interface module 603 for communicating with the athletic information collection and display device 501. As previously noted, the athletic information collection and display device 501 may communicate with the athletic data display configuration device 601 through a conventional network, such as the Internet. With these configurations, the interface module 603 may be implemented using any conventional type of network interface, such as a network interface card. Of course, any type of desired hardware or software combination alternately may be used to allow the athletic data display configuration device 601 to communicate with the athletic information collection and display device 501.

The athletic data display configuration device 601 also includes an athletic data display configuration module 605, and an athletic data storage 607. When the interface 603 of the athletic data display configuration device 601 receives athletic data from the athletic information collection and display device 501, it provides the received athletic data to the athletic data display configuration module 605. The athletic data display configuration module 603 may then store the athletic data in the athletic data storage 607 for future use. As will be discussed in more detail below, the athletic data display configuration module 605 also will retrieve athletic data from the athletic data storage 607, and configure the retrieved athletic data for display through one or more user interfaces in a manner that is meaningful to a user.

Returning now to FIG. 5, when a user wishes to view information relating to his or her athletic activities (or the athletic activities of another, as will be discussed in more detail below), the user submits this request to the athletic information collection and display device 501. More particularly, the user can employ conventional input and output devices, such as a keyboard, mouse, display and the like. The display request is then provided to an athletic data display module 509 through a conventional interface input/output interface 511. As well known in the art, the interface input/output interface 511 may be implemented using any desired combination of hardware and software components, such as conventional application programming interfaces (APIs) used to detect and process input from input devices, and to send data to and otherwise control output devices.

With some examples of the invention, the athletic data display module 509 may be implemented using any conventional tool for receiving input to request and control the display of data, and then subsequently displaying the data in the manner requested. For example, the athletic data display module 509 may be implemented using a conventional browser program, executing on a computing device, such as device 114. In still other embodiments of the present disclosure, the athletic data display module 509 may be implemented by, for example, a purpose-specific software tool for displaying athletic data. In yet still other embodiments of the present disclosure, the athletic data display module 509 may generate an interface that is provided to the user via one or more series of webpages (e.g., a website).

As will be discussed in more detail below, when a user activates the athletic data display module 509, he or she is provided with a user interface prompting the use to select what collected athletic data he or she wishes to view, the format in which the user wishes to view the collected athletic data, etc. This user interface may be generated by the athletic data display module 509, the athletic data display configuration module 605, or some combination thereof. When a user employs the provided user interface to submit a request to view athletic data, the athletic data display module 509 relays the request to the athletic data display configuration module 605. In response, the athletic data display configuration module 605 configures the requested athletic data for display by the athletic data display module 509. For example, as will be discussed in more detail below, a user may request to view a total amount of athletic activity performed by a user over a period of time, such as the athletic activity performed each day in a one week period. In response, the athletic data display configuration module 605 will retrieve the relevant athletic activity data from the athletic data storage 607. It will then configure the retrieved athletic activity data to be displayed through a desired image (e.g., a graph), and provide the configured athletic data to the athletic data display module 509 for display to the user.

It should be noted that, with some embodiments of the invention, the data display configuration functions may be divided between the athletic data display module 509 and the athletic data display configuration module 605. For example, if the athletic data display module 509 is implemented by a simple browser, then the athletic data display module 509 may serve as a "thin client" for the athletic data display configuration module 605. That is, all of the data display configuration functions may be performed by the athletic data display configuration module 605. The athletic data display module 509 will then only display the information provided to it. Alternately, if the athletic data display module 509 is implemented by a purpose-specific software tool, then most or all of the data display configuration functions may be performed by the athletic data display module 509. With these examples, the athletic data display configuration module 605 may be used only to store and retrieve athletic data from the athletic data storage 607.

Figure 7:
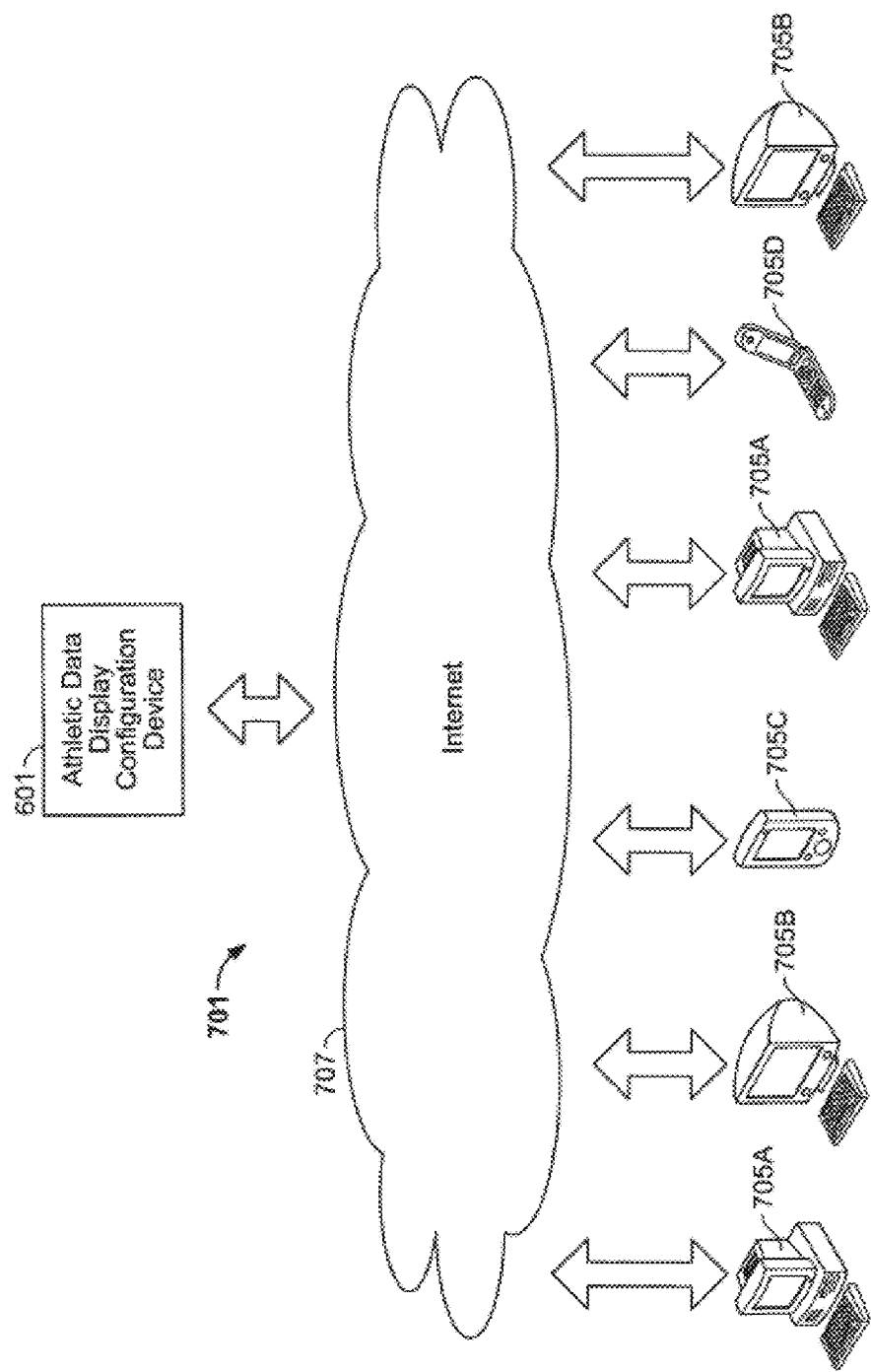
FIG. 7 illustrates a network including an athletic data display configuration device and a plurality of client devices of the type that may be employed according to various examples of the invention.

Typically, the athletic data display configuration device 601 will be implemented at a remote location from the athletic information collection and display device 501. The athletic information collection and display device 501 then may be connected to the athletic data display configuration device 601 through an electronic communication network, as previously noted. The electronic communication network may be a public network, such as the Internet, a private network, or include some combination of both. For example, FIG. 7 illustrates a network 701 including an athletic data display configuration device 601 and a plurality of client devices 705 for collecting and/or displaying athletic data. These client devices 705 may include various types of computing devices (e.g., devices 705A-D), such as laptops, personal computers, tablets, mobile computing devices, etc. Of course, various examples of the invention may alternately or additionally include any other desired electronic device that can be configured to collect and/or display athletic data as discussed above.

It should be appreciated that a client device 705 may perform an athletic data collection function, an athletic data display function, or both. That is, while the example of the athletic information collection and display device 501 described above is capable of both collecting and displaying athletic data, some client devices 705 may only collect athletic data. Further, some client devices may only display athletic data. For example, a user may employ a GPS-equipped smart telephone to collect athletic data and transmit the collected athletic data to the athletic data display configuration device 601. The user may then employ a personal computer equipped with only a conventional browser to subsequently download and display the collected athletic data.

II. Visualization of Athletic Activity

Figure 8:
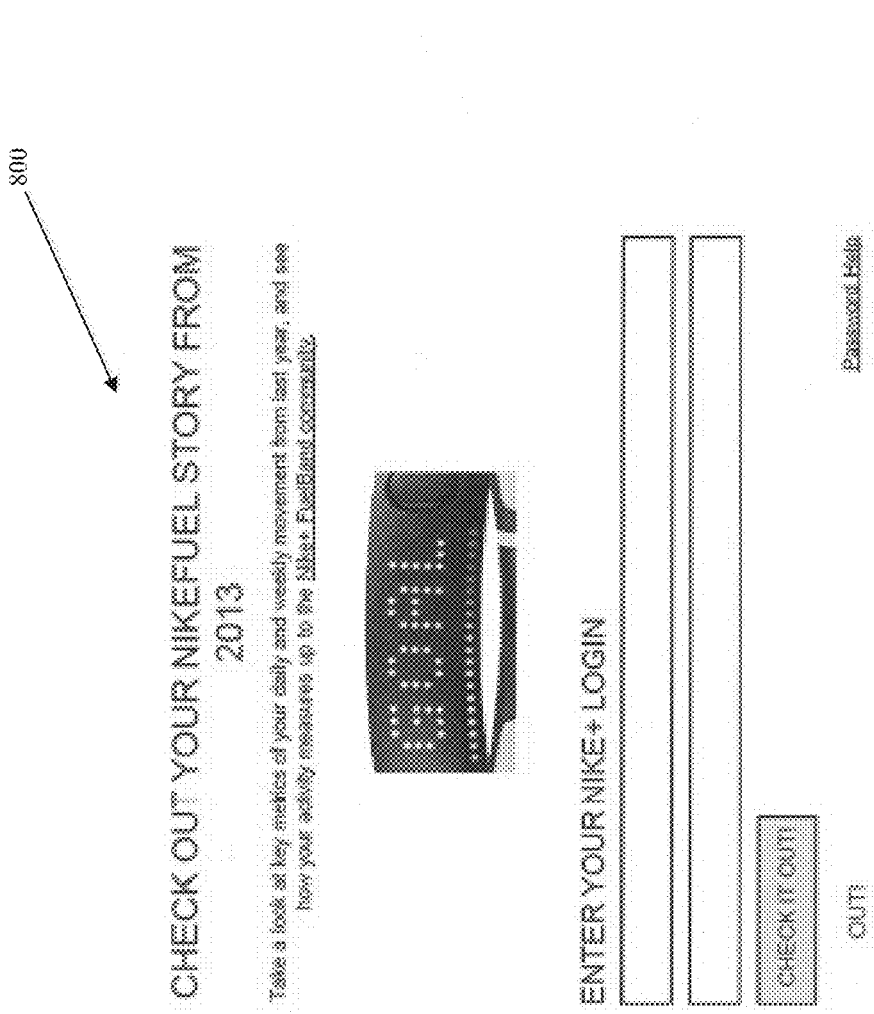
FIG. 8 shows an example display of a login interface presented by a display screen of a computer device in accordance with example embodiments.

In response to receiving a request to review athletic information from a user via the athletic data display module 509, the athletic data display configuration module 605 may determine or confirm the user's identity. FIG. 8 illustrates an example of a user interface response that might take place as a result of a user requesting to review athletic information. In this illustrated example, a login interface may be presented to the user. Login interface 800 may include an overlay screen portion or text box(es) that request information from the user in order to view their athletic information. For example, as illustrated in FIG. 8, text boxes may be displayed in a portion of login interface 600 that request entry of the user's account login and password. The request(s) for information may be provided to the user in any desired manner or format without departing from the present disclosure, such as via text input boxes, drop down listings, etc.

In some embodiments, one or more text boxes displayed in login interface 800 may be pre-populated with the requested user information. For example, if a user has previously created a user account with the entity offering maintaining (or storing) the users athletic information (e.g., a Nike+ account), the athletic data display configuration device 601 may retrieve the requested user information from a cookie (or other data storage), and display the user information in the one or more text boxes when the login interface is initially displayed to the user. Once all necessary or desired information is input by the user, the user may select the "Check It Out" icon (or in any other desired manner) to access their collected athletic information. Optionally, if desired, the user may access their collected athletic information without the need for input of this type of additional registration information, without departing from the present disclosure. This may be done, for example, if account information for the user (e.g., username, email, password, etc.) and/or other user ID information has already been stored (e.g., in a cookie).

If a user does not have a user account, the user may register for a new user account. The user may be provided with a registration interface that requests information from the user in order to generate a user account. For example, the registration interface may include text boxes that request entry of the user's name, email, a user ID, password, gender, zip code, mobile phone number, and other desired information. In this example, the system may store this information for subsequent use.

After the athletic data display configuration module 605 has confirmed the user's identity, the athletic data display configuration module 605 may then retrieve the athletic data associated with the user from the athletic data storage 607. Next, the athletic data display configuration module 605 may prepare a user interface for displaying the requested athletic data, and transmit the user interface with the athletic data to the athletic data display module 509 for display to the user.

Figure 9A:
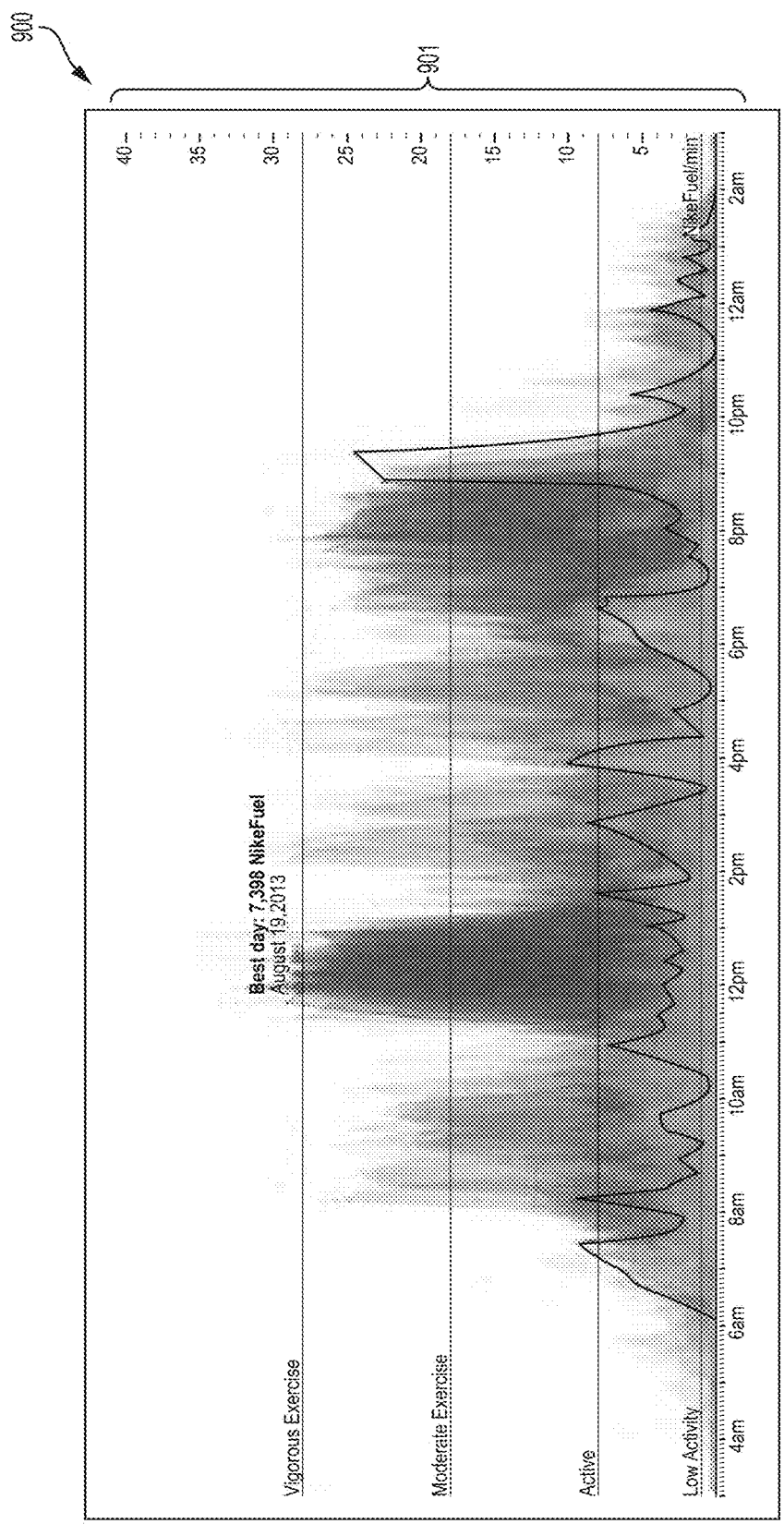
FIG. 9A shows an example display of an activity data interface presented by a display screen of a computer device in accordance with example embodiments.
Figure 9A:
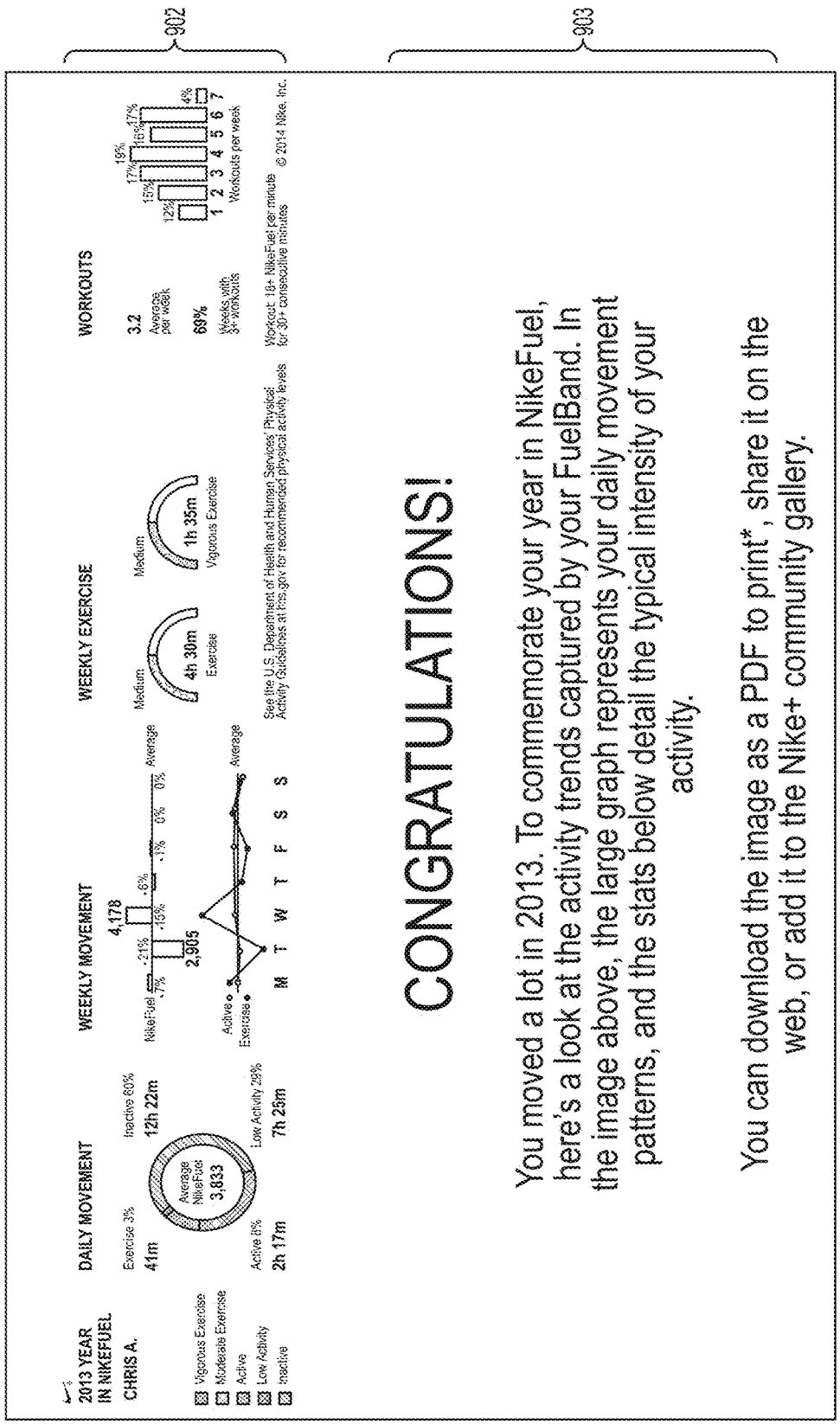

FIG. 9A illustrates an example of an initial user interface that may be provided to a user according to various implementations of the invention. As seen in this figure, a potion 901 of the user interface 900 includes a graph illustrating athletic information for the user over a specified time period. As will be appreciated, a user's athletic activity may be displayed using various other types of graphics, such as charts, maps, etc. A second portion 902 of the user interface 900 includes a plurality of interactive sub-interfaces (or interface elements), each representing athletic data values corresponding to athletic activity performed by the user over the specified time period. As will be described in more detail below, the various sub-interfaces (or interface elements) in portion 902 of the user interface 900 may also display or provide athletic activity metrics to the user based on the athletic activity performed by the user over the specified time period. A third portion 903 of the user interface 900 may include a textual message to the user related to the athletic information provided in interface portions 901 and 902. For example, as illustrated in FIG. 9A, portion 903 displays a message describing and explaining the athletic information presented to the user in interface portions 901 and 902. As will be appreciated, various types of textual messages may be provided to the user in accordance with the athletic information presented in user interface 900. In some aspects of the disclosure, interface portion 900 may provide a message explaining the information displayed by a particular user sub-interface (or interface element) in portion 902. For example, hovering a user input element (e.g., a mouse pointer or other selection input element) over any of the sub-interfaces (or interface elements) or portions of the activity graph may provide further information in portion 903 of interface 900. For example, portion 903 may display information such as a name of a place, an amount of athletic activity performed at that point, activity points earned, terrain type, speed and the like. As another example, portion 903 may display information explaining the particular activity metric being measured by a selected interface element in portion 902 of the interface.

As will be appreciated, in some aspects of the present disclosure, the device utilized by the user to view the athletic activity data may be equipped with a touch-sensitive display screen configured to recognize one or more physical gestures performed by the user as user input. For example, the device may recognize an upward finger swipe performed by the user on the touch-sensitive display screen as user input corresponding to an upward scroll. Accordingly, upon recognizing this user gesture, the device may scroll the interface being displayed on the device display upward. As another example, the device may recognize a single tap on the display screen as a user input selection. The user may also rotate, swipe, tap, or pinch the device display as a means of inputting data or selecting options and/or interface elements within the interface display. Any suitable method of inputting data or selecting options within the interface display may be implemented without departing from the present scope of the disclosure.

Figure 9B:
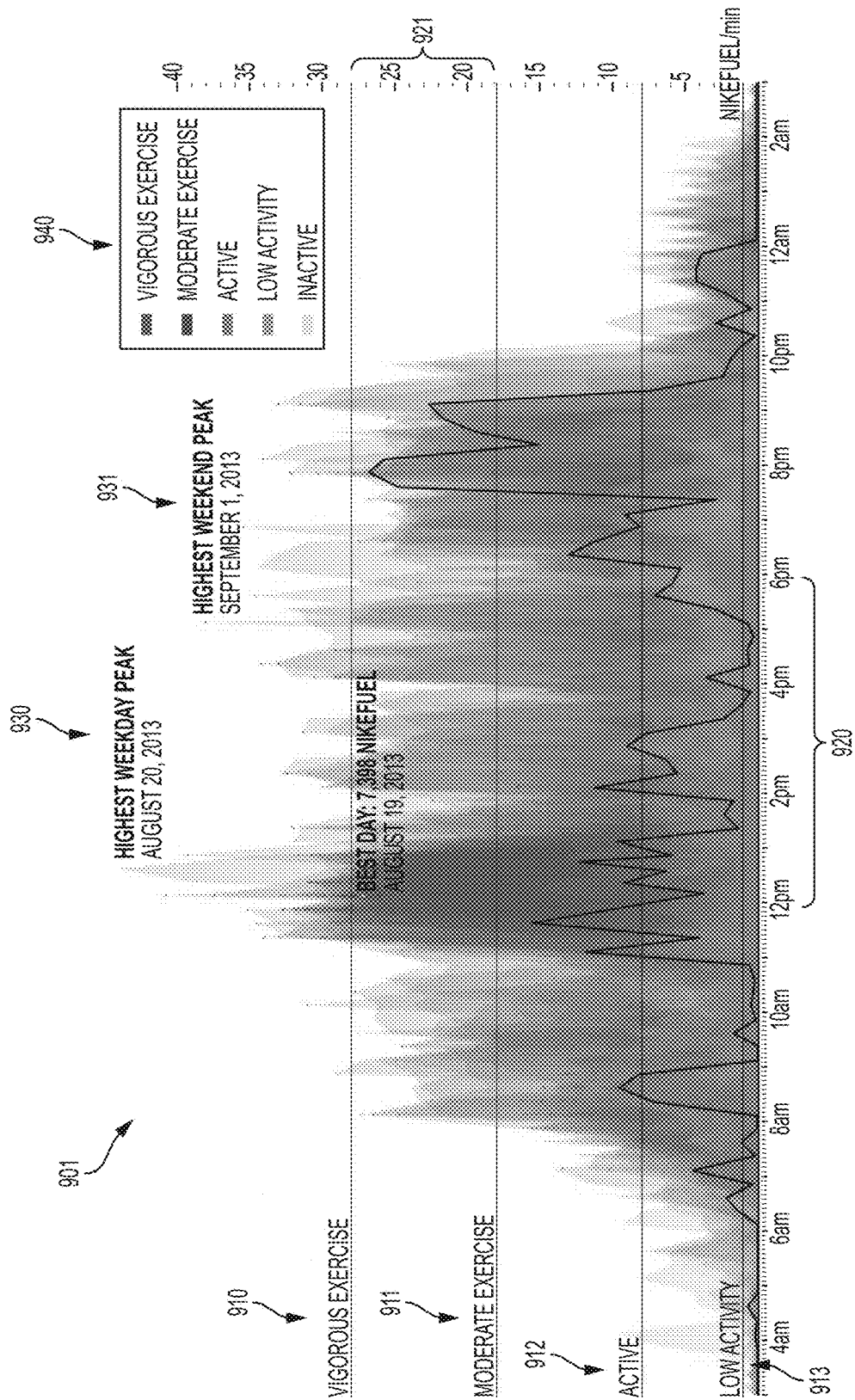
FIG. 9B shows an example display of a portion of an activity data interface presented by a display screen of a computer device in accordance with example embodiments.

As discussed above, one or more interfaces described herein may be configured as a widget or a website. In one or more configurations, the website function may be provided as a series of webpages, applets or combinations thereof. With some implementations of the invention, athletic data relating to a single person is collected and displayed so that the person can fully critique his or her performance. For example, FIG. 9B illustrates an example display of interface portion 901 that may be presented to the user via a website. In this example illustration, interface portion 902 displays athletic activity data expressed in terms of activity points or energy expended by the user over a specified period of time.

As shown in the example interfaces in FIG. 9B, a set of athletic data corresponding to athletic activity performed by a user over a first time period may be displayed as a graph (e.g., athletic activity graph). The athletic information displayed within the athletic activity graph may correspond to athletic activities performed by a person over one or more time periods. For example, referring to FIG. 9B, the athletic activity data collected for a user over the course of a year may be shown within the interface with respect to a time of day the athletic activity was performed. In this example, the x-axis of the graph represents a particular time of day within a 24 hour period. For example, element 920 in FIG. 9B represents a 6 hour period of time from Noon to 6 pm. Accordingly, the portion of the activity graph corresponding to element 920 represents all of the activity data collected for a user over the past year, each day, between the hours of Noon and 6 pm. As will be appreciated, the user may adjust or modify the time period for which athletic activity is displayed in the interface. For example, the user may want to view athletic activity data collected for a particular time period (e.g., 1 day, 1 week, 1 month, etc.).

Referring back to the example interface in FIG. 9B, in this example, the y-axis of the graph may represent an amount of athletic activity performed by the user. The values displayed in the y-axis of the graph may be based upon a user's performance of physical activity and relate to, for example, energy expenditure, activity points, intensity, as well as other values. In some aspects of the present disclosure, the amount of athletic activity performed by a user may be indicated as a number of activity points earned by a user over time. For example, a user may be awarded a predetermined number of activity points for running a predetermined distance, or for performing a particular amount of athletic activity. In other aspects of the present disclosure, the amount of athletic activity performed by a user may be indicated as a rate of activity points earned by a user over time.

As shown in FIG. 9B, the athletic activity graph may be segmented into activity thresholds based on the amount of activity performed by the user. In this example, the graph displays 5 different thresholds, each representing a specified level of athletic activity performed by the user. For example, in the instance that the y-axis of the graph represents a number of activity points earned per minute, the "Moderate Exercise" threshold corresponds to athletic activity performed by a user when the user earned (or achieved) between 18 and 28 activity points/min. As another example, the "Vigorous Exercise" threshold corresponds to athletic activity performed by a user when the user exceeded 28 activity points/min. As will be appreciated, any number of activity thresholds may be displayed in the interface to indicate different amounts of athletic activity performed by the user without departing from the scope of the present disclosure.

Additionally or alternatively, the athletic activity data presented in the interface may be visualized in a variety of ways. For example, an athletic activity graph may be represented by a data-point graph having various textures, colors, patterns and the like. The various patterns, colors or textures may also be used to represent different information attributes such as a time of day, proximity to athletic goal, or level of intensity of a particular set of activity data. The various colors, textures and patterns may be generated in a manner to facilitate a user identifying or discerning the athletic data represented in the graph or chart. For example, as illustrated by the legend (element 940) in interface 101, the athletic activity graph may be color coded based on the amount of athletic activity performed (e.g., rate of activity points earned) by the user. In this example, athletic activity performed by the user that falls within the threshold of "Vigorous Exercise" performed may be represented in the athletic activity graph by the color blue. Similarly, athletic activity data within the "Moderate Exercise" threshold may be represented by the color purple, (etc., "Active" as red; "Low Activity" as orange; and "Inactive" as yellow).

In some aspects of the present disclosure, interface portion 901 may display activity milestones or achievements reached by the user during the athletic activity time period represented in the athletic activity graph. The interface may further include one or more indicators identifying certain events of the user's activity during a particular time period. For example, times corresponding to the user's highest or best values with respect to one or more metrics may be marked within the interface (e.g., activity graph). Indicators may be color coded and/or labeled to provide some information about what is being marked. According to one aspect, if a user selects a portion of the activity graph (rather than the entire activity graph), the indicators may be modified to reflect and identify the best (e.g., highest or lowest) metric values measured for the user during the selected portion. For example, the system may automatically determine the best metric values for the selected portion of the activity session.

As illustrated by element 930 in FIG. 9B, the interface may identify athletic activity data for the user corresponding to the day and time in which the user gained the most athletic activity points on a week day (e.g., Aug. 20, 2013 at 12:15 pm). As another example, as illustrated by element 931 in FIG. 9B, the interface may identify athletic activity data for the user corresponding to the highest peak in athletic activity points gained by the user on a weekend (e.g., Sep. 1, 2013 at 5 pm). As will be appreciated, various types of milestones or achievements may be identified in the athletic activity data displayed in the interface without departing from the scope of the disclosure.

Athletic activity data may further be published in one or more outlets. The interface may provide the user with various tools or interface elements (or icons) that permit the user to share their performance metrics and athletic activity data with other users and/or to post to a social networking website. The user may also input a message (e.g., "check out my Year-in-Fuel") to accompany the performance metrics and data being sent. The computer 114 (or other computing device) may distribute performance metrics and athletic activity data of a current and/or previous activity session and the message to another computing device (e.g., server 111) in response to a user's request to share. The server 111 may incorporate the data and/or message in the social networking web site and/or may distribute the data/message to other desired or all users. As yet another example, activity data may be published as a news entry on a user's social network page. Alternatively, the activity data may be published as a status entry on a user's social messaging site. The user may further limit the types and/or amount of information publicly displayed.

In some aspects of the present disclosure, the athletic data display configuration module 605 may process and analyze athletic data requested by a user for display to generate various performance metrics. The athletic data display configuration module 605 may prepare a user interface (or a portion of a user interface) for displaying the performance metrics associated with requested athletic data, and transmit the user interface with the athletic data and performance metrics to the athletic data display module 509 for display to the user. In some aspects of the present disclosure, as shown in FIG. 9A, the generated performance metrics may be displayed simultaneously with the graph. As shown in FIG. 9A, interface portion 902 may include one or more sub-interfaces (or interface elements) indicating the various performance metrics generated for the athletic activity information displayed in interface portion 901. Each sub-interface (or interface element) may represent athletic data metrics corresponding to an athletic activity performed by the user over a specified time period.

For example, referring to FIG. 9C, user interface portion 902 may include a "Daily Movement" sub-interface that displays what percentage of the day a user spends performing various athletic activities and the activity threshold category that the activity corresponds to (e.g., active, low activity, etc.). In some embodiments, the "Daily Movement" sub-interface may display an average amount of athletic activity performed by the user over a plurality of time periods (e.g., days). In some aspects of the present disclosure, the interface may receive a user input selection indicating the particular day for which the user desires to view athletic activity information within the "Daily Movement" sub-interface. In some aspects of the present disclosure, the one or more icons and/or graphics illustrated in the "Daily Movement" sub-interface may be continuously updated (e.g., in real-time) to display the athletic activity data corresponding to a user input selection of one or more areas of the athletic activity graph. The user may interact with one or more sub-interfaces to request and/or display desired athletic activity data and performance metrics. This may allow the user to better understand his or her progress and improvement (if any) during various activity sessions and performances displayed in the interface.

As another example, referring to FIG. 9D user interface portion 902 may include a "Weekly Movement" sub-interface that displays an amount of athletic activity performed by the user over the course of a week as compared to the average amount of athletic activity performed by the user over a first time period. This exemplary sub-interface may also display percentage gains/losses in the amount of activity points, per day, that were earned by the user. Other performance metrics may be displayed in sub-interfaces without departing from the present scope of the disclosure, such as "Weekly Exercise" (see FIG. E), and "Workouts" (see FIG. F), which may represent various athletic data metrics corresponding to an athletic activity performed by the user over a corresponding time period. Additionally or alternatively, other performance metrics than the ones shown in FIGS. 9C-F may include a total number of jumps, a number of vertical jumps above a certain height (e.g., above 3 inches), a number of sprints (e.g., speed above a certain rate), a number of fakes (e.g., quick changes in direction), a jump recovery (e.g., a fastest time between two jumps), a work rate (e.g., may be a function of average power multiplied by time length of a workout session), a work rate level (e.g., low, medium, high), total steps, steps per unit time (e.g., per minute), number of bursts (e.g., number of times a user exceeds a speed threshold), average time duration of workout sessions, total session time, average number of repetitions per exercise, average number of points earned per workout session, total number of activity points earned, number of calories burned, or other performance metrics. Additional performance metrics may also be used.

Some implementations of the invention may alternately or additionally allow a user to passively compare his or her athletic data with other users. For example, in some aspects of the present disclosure, the user may access a Gallery of other activity graphs corresponding to the athletic data of one or more other users within a community (e.g., friends, a group in which the user is a member, all members of the website). A user may easily discern the performance of another user by viewing their corresponding athletic activity graph that visually represents the user's athletic activity performed over a period of time. A user may scroll through the gallery of athletic activity graphs, via user input, in one or more directions to view additional graphs not currently displayed on the interface.

As noted above, a user's athletic data may be depicted within an athletic activity graph using various textures, colors, patterns and the like, wherein the various patterns, colors or textures may also represent different information attributes. As another aspect of this invention and as illustrated by element 1002 in FIG. 10A, a user's athletic data may be depicted as a unique emblem, insignia, or other design to illustrate a visual microarray of the user's athletic data or performance (e.g., amount of activity points earned) over a predetermined time period.

Figure 10A:
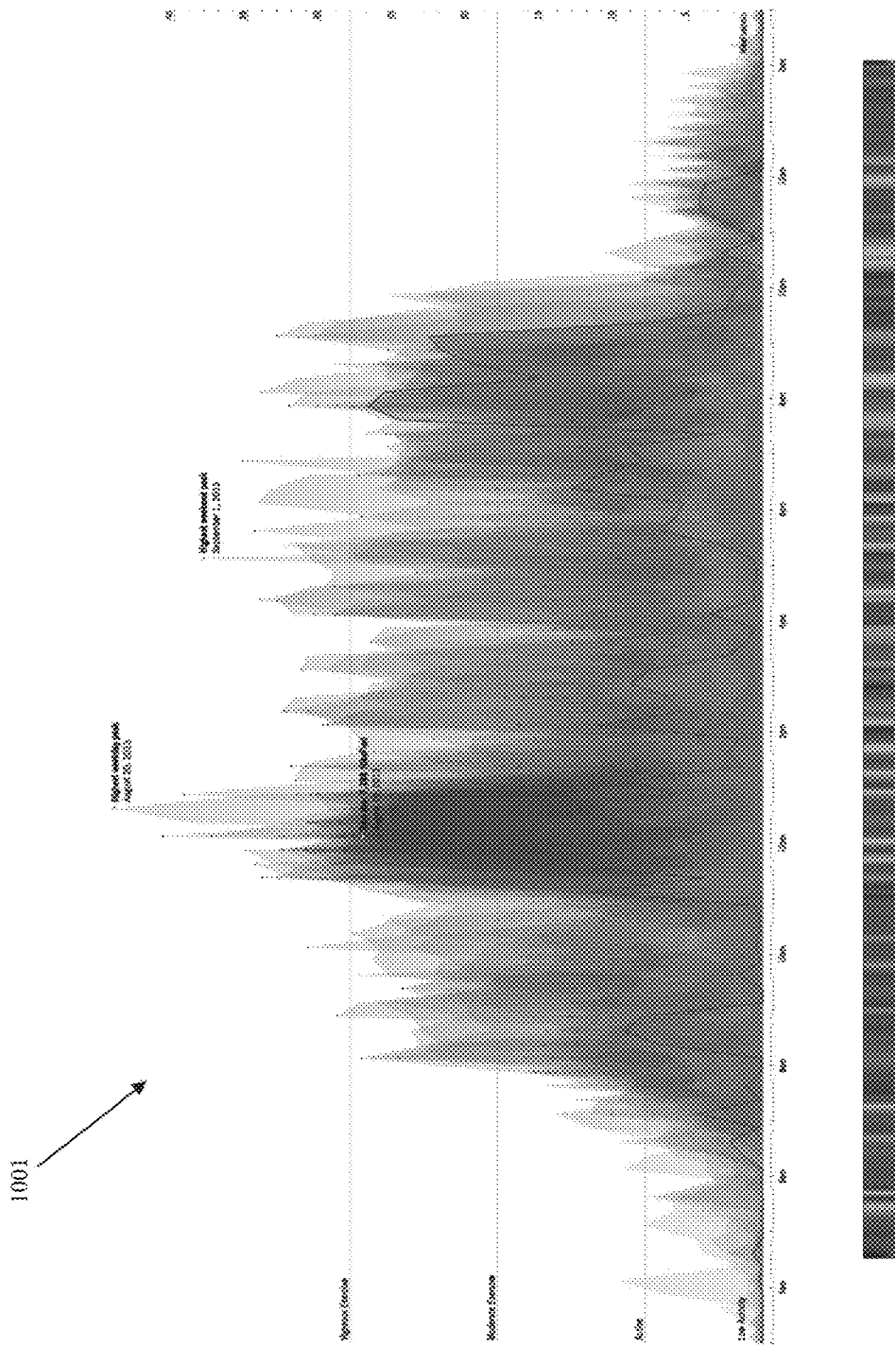
FIG. 10A-B shows an example display of athletic activity and corresponding activity designs in accordance with example embodiments.

In some aspects of the disclosure, the system may generate the activity design to depict athletic activity data for a user over the course of a first predetermined time period (e.g., a week, a month, a year, etc.). For example, as shown in FIG. 10A, activity design 1002 represents the athletic activity data displayed in interface 1001. In this example, activity design 1002 is comprised of 365 separate visual elements, each element representing a specific amount of athletic activity performed by the user for a second predetermined time period (e.g., a day) over the course of the a first time period (e.g., 1 year). The system may be configured to assign and/or store a specific array value to each element of a generated activity design. For example, the system may determine an average number of activity points (or rate of activity points) earned by a user over the course of the second time period (e.g., a day), and store that value in memory. In other embodiments, the system may store in memory values associated with other performance metrics corresponding to athletic activity performed by a user without departing from the scope of the present disclosure, such as a total number of activity points earned, a total number of activity points earned within a third time period (e.g., number of hours), average activity points accrued over a predetermined unit of time measurement (e.g., average points/min), etc.

One or more algorithms or equations utilized in various calculations may include derivations of measured and/or calculated activity point values. Derivations that include time periods, such as energy expenditure or activity points per unit of time may be used to show rates and rates of change in athletic activity performed by a user. For example, one equation may be used to determine a rate of accumulating activity points or energy expenditure values. For example, sensor data, including one or more force sensors configured to be placed within or on a user (or their footwear, apparel, etc.), may be used to determine a user's speed, cadence, distance, pace, and/or energy expenditure. One or more algorithms, which may be stored as computer-executable instructions on a tangible computer-readable medium, may be implemented to determine a quantity of activity points or energy expenditure points accumulated over a predetermined time period and/or only upon certain levels of detected activity.

Figure 10B:
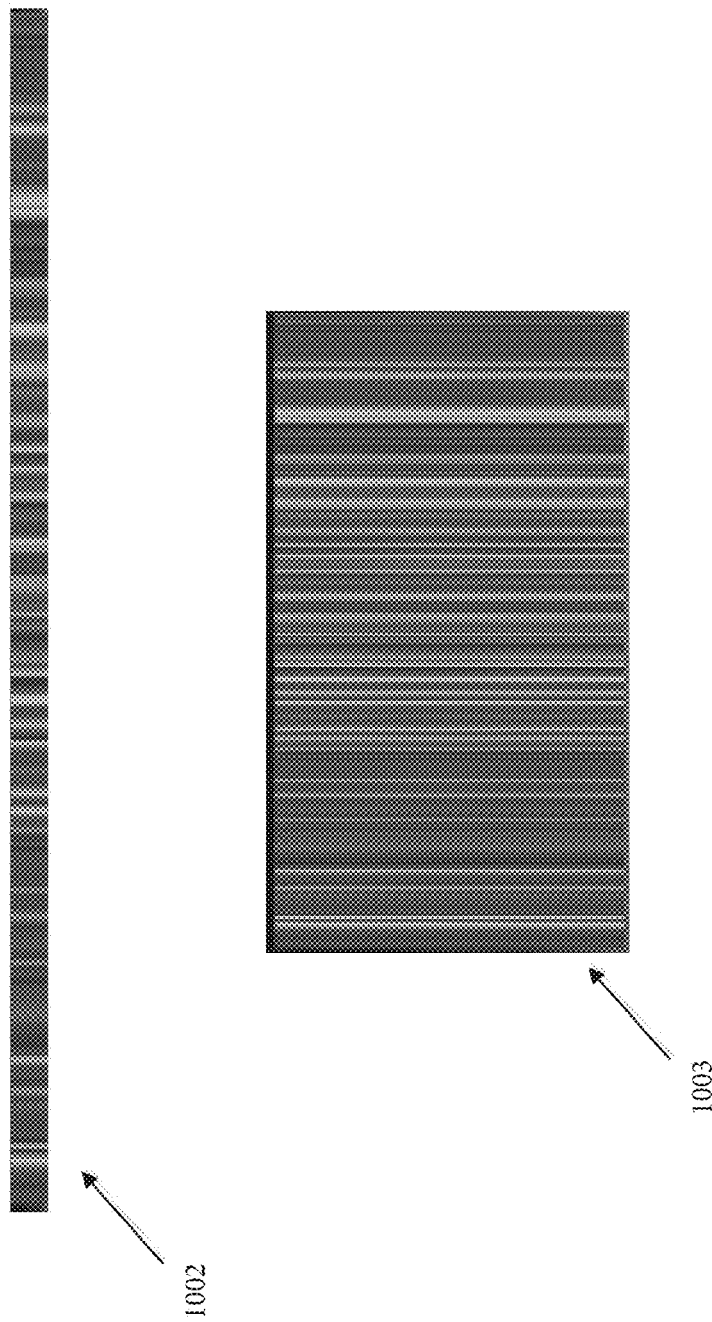

The system may then determine a particular color value in the RGB color space for an element in an activity design based on a corresponding stored performance metric for the user. For example, in the instance that an activity design comprises 365 elements (i.e., each element represents one day in a year), for a first element in the activity design, the system may retrieve a value corresponding to a first performance metric (e.g., activity points/min) for the user during a particular time period (e.g., 9 am to Noon) for the first day of a year selected by the user (e.g., Jan. 1, 2013). As will be appreciated, the system may be configured to retrieve activity point values for a user based on any number of performance metrics or time periods. In some embodiments, the system may receive user input identifying the performance metric and/or the period of time for which activity point values for an activity design are to be determined. In some aspects of the disclosure, the system may multiply the retrieved activity point value by a scalar (e.g., a Hex value) prior to determining or assigning a corresponding RGB color value. The system may continue to determine and/or assign RGB color values for each element in the activity design based on retrieved activity point values for a user. After RGB color values have been assigned to each element in the activity design based on corresponding retrieved activity, the system may generate a display of the activity design based on the assigned color values. For example, as illustrated by element 1003 in FIG. 10B, the displayed activity design comprises 365 elements, each element having a unique color corresponding to an assigned RGB color value based on athletic activity performed by a user over the course of a year, e.g., the athletic activity data shown in interface 1001.

Figure 11:
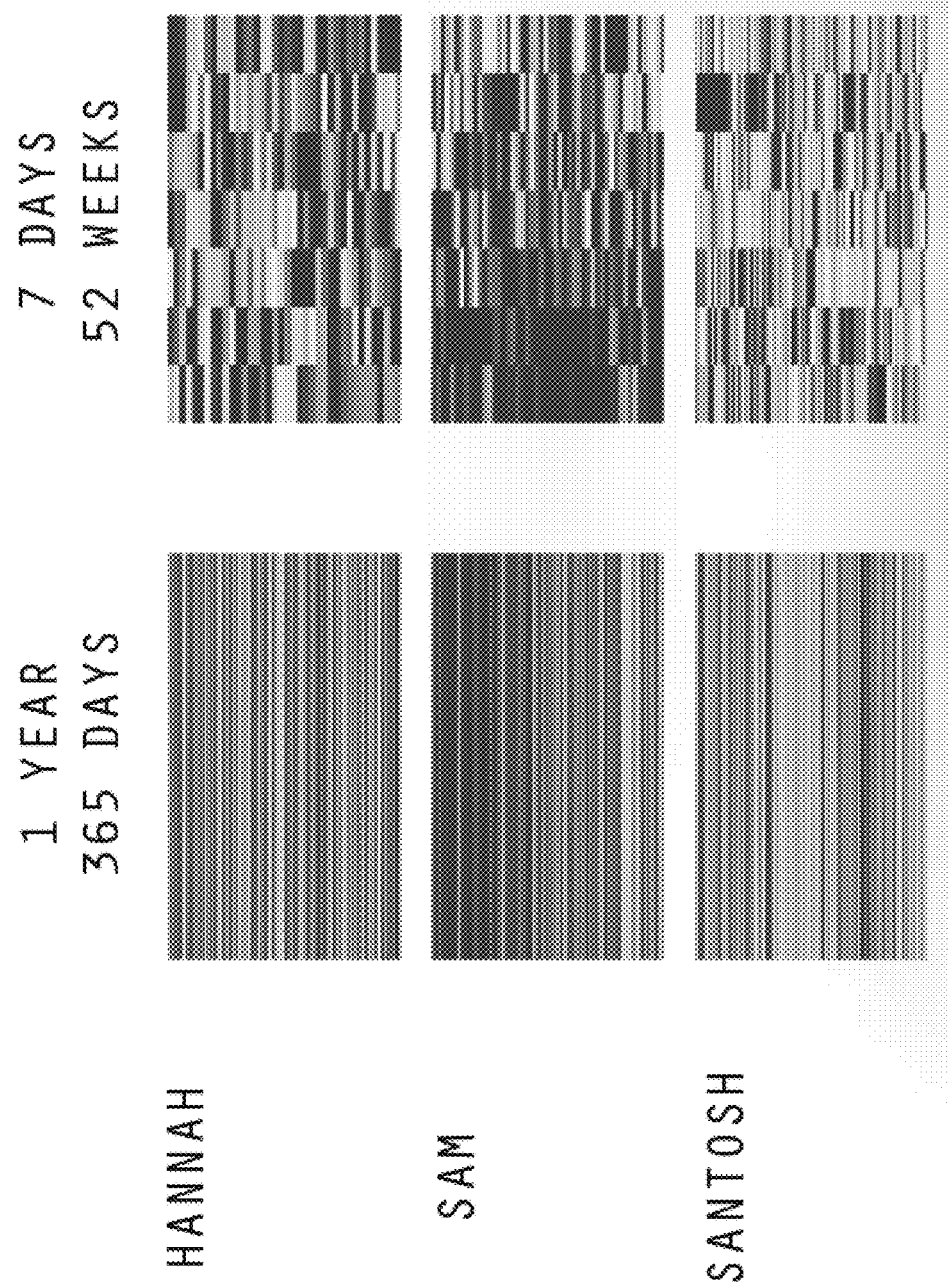
FIG. 11 shows example activity designs in accordance with example embodiments.

The system may generate the activity design based on assigned RGB color values in a number of ways without departing from the scope of the disclosure herein. For example, referring to FIG. 11, a first type and a second type of example activity design is shown for three different users (e.g., Hannah, Sam, and Santosh) based on their respective athletic activity data. The first and second types of activity designs both illustrate athletic activity data for a user over the course of a year, but display this data utilizing different segmentations. As shown in FIG. 11, the first type of activity design illustrates athletic activity data for each day over the course of a year (e.g., 365 day). By contrast, the second type of activity design illustrates athletic data segmented in a manner to depict the daily athletic performance of the user over the course of seven days for 52 weeks. As shown in FIG. 11, each type of activity design has a particular structure of elements that comprise the generated design. As will be appreciated, and as illustrated FIG. 11, the activity design pattern corresponding to (e.g., visualizing) a user's athletic data may vary in accordance with the specified time period. A user may be provided, via the interface, with an option to select the particular type (e.g., element structure, design pattern) of the activity design that they desire.

Figure 12:
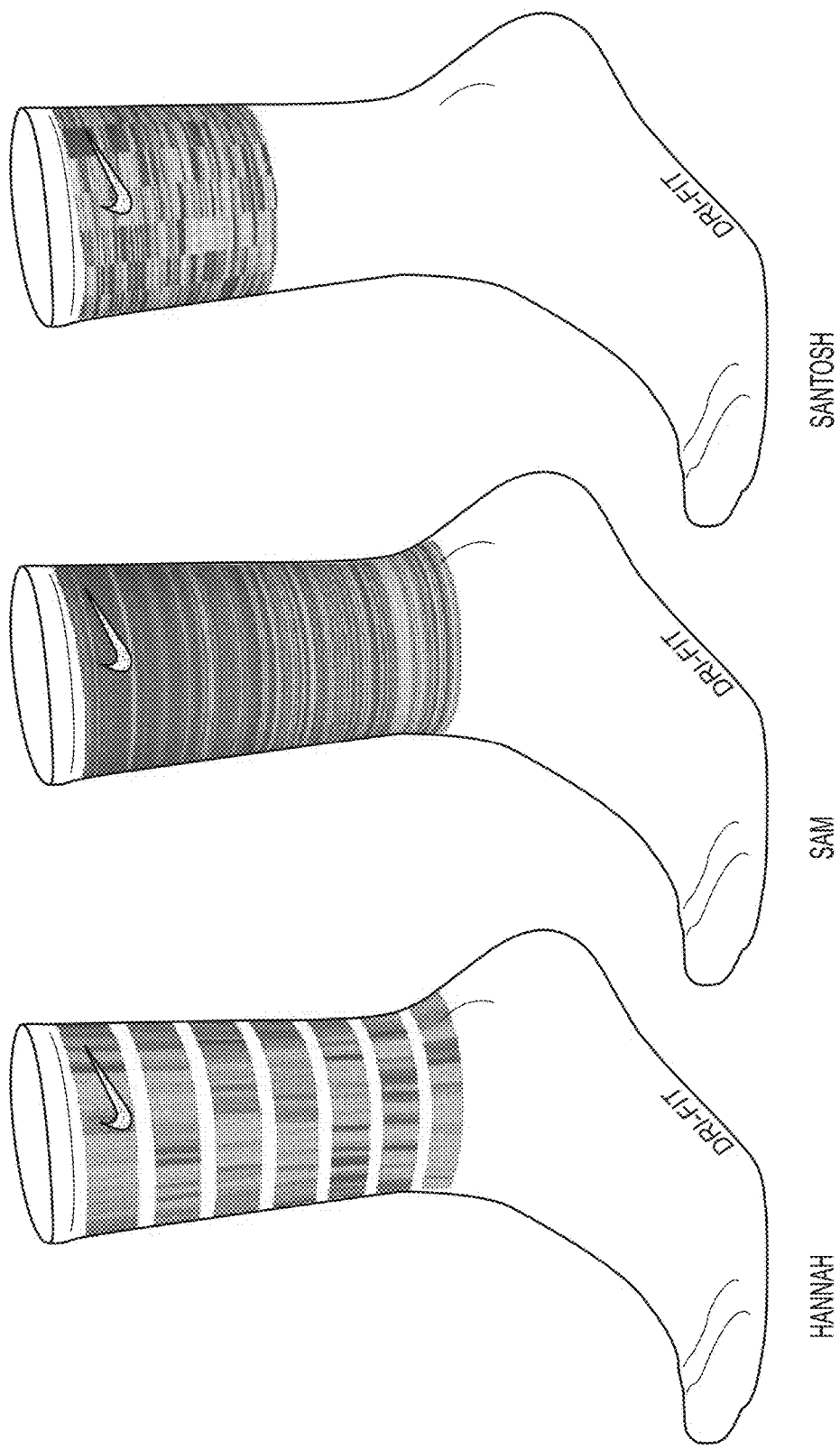
FIG. 12 shows example footwear products displaying activity fingerprints in accordance with example embodiments.

The emblem, sigil, insignia, or other activity design depicting a user's athletic data or performance over a predetermined time period may be included in apparel, footwear, or other custom designed products purchased by the user. For example, as illustrated in FIG. 12, generated activity designs may be included on socks, sweatshirts, shoes, or other types of apparel. As discussed above, each activity design may be unique to the user whose athletic data was used to generate the activity design. Accordingly, the activity design may be used as a visual or digital athletic signature (e.g., fingerprint, watermark) to identify a user within the community of users. In some aspects of the present disclosure the system may utilize the generated activity design as a digital athletic signature (e.g., watermark, fingerprint) for the purpose of confirming or validating a user's identity. For example, as described above with reference to the log-in interface illustrated in FIG. 8, the system may display a one or more generated activity designs, and may prompt the user to select their personal activity design from the plurality of displayed activity designs.

In some aspects of the disclosure, a generated activity design for a user may be updated continuously (e.g., in real-time) or on a specified schedule (e.g., daily, hourly, etc.). Continuous and/or periodic updating of a generated activity design for a user provides additional security measures for the user. The amount of athletic activity performed by a user at any given time is unique to that particular user. Additionally, the user may have the option of selecting the particular performance metrics used to generate their personal activity design. The user may also have the option of selecting the one or more time periods of athletic activity data used by the system to generate the user's unique activity design. Consequently, each user's generated activity design may be customized or tailored to a user based in part on an amount of athletic activity performed and the time period in which the activity was performed. By constantly (or periodically) updating the color and/or type (e.g., element structure, design pattern, etc.) of the activity design based on user athletic activity data and personal preferences, the activity design provides superior security measures against potential counterfeiters. Each generated activity design may represent a unique, and in some instances, dynamically shifting visualization of a user's athletic activity data, and may also be used to validate or confirm the user's identity.

In other aspects of the disclosure herein, an activity design generated for a user may be stored in a database and associated with the user's account or profile. The system may continuously or periodically update the activity design stored for a user in accordance with activity data received from one or more athletic monitoring devices associated with the user. The system may be configured to retrieve and/or transmit the activity design to one or more other computing devices. In some aspects of the present disclosure, the system may transmit to a computing device, wirelessly or otherwise, data identifying and/or relating to a generated activity design. For example, the system may transmit data identifying the activity design type (e.g., element structure, design pattern), and the RGB color values for each of the individual elements comprising the activity design. Such information may be encrypted by the system using well-known encryption techniques, and transmitted to a computing device, such as a wearable monitoring device. Additionally or alternatively, the system may receive a request for activity design data from a computing device, such as a wearable monitoring device operatively connected to or in communication with the system.

In some aspects of the disclosure herein, other methods of identifying and/or validating a user's identity may be utilized in conjunction with activity design data generated by the system. In some example embodiments, the process of validating a user's identity based on their unique activity design (e.g., digital athletic signature), as discussed herein, may comprise the first step of a multi-step validation process. As will be appreciated, other well-known validation methods may be used in conjunction with and/or in addition to the activity design validation process described herein. For example, a user may be prompted to provide biometric information, via a biometric fingerprint (or heartbeat) sensor to confirm their identity.

In some aspects of the present disclosure, the verification methods discussed above may be used within a retail environment. For example, the system may be operatively connected to and/or in communication with one or more payment servers or other computing devices associated with a user's payment or financial account (e.g., bank account, credit card account, etc.). At the point of purchase, a user may be prompted to verify their identity prior to purchasing a product or processing a payment transaction. The retail store may have a remote system configured to communicate with a payment server or other computing device associated with a user's payment or financial account.

The remote system may include various components, elements, or characteristics without departing from the invention. For example, the remote system may include a display device for displaying information based at least in part on data transmitted by the device associated with the user. Additionally or alternatively, the remote system may include another data transmission system, e.g., for transmitting data to another independent system or device, such as the device associated with the user (e.g., mobile computing device, wearable monitoring device, etc.). As will be discussed in more detail below, the remote system may receive data identifying the activity design for the user, and the remote system may use this information to confirm or validate the identity of the user. In other aspects of the present disclosure, the remote system may utilize a user's activity design data to activate specific advertisements or product information to be displayed to the user, e.g., directed to this specific product line and/or related products.

The computing device associated with the user, such as a mobile computing device or wearable monitoring device, may have stored in memory current activity design data for the user. The computing device may be configured to transmit data to the remote computer system at the retail location using one or more types of wireless communication (e.g., near-field communication, Bluetooth, infrared, etc.). The remote system may be configured to capture the activity design data transmitted from the device associated with the user and transmit that information to one or more payment servers. The transmitted activity data may be processed by the payment server for the purpose of confirming or validating the user's identity.

In some embodiments, a payment server may determine whether the activity design data transmitted from a remote system at a retail location corresponds to activity design data stored in another computing device, such as athletic data display configuration device 601. This may be accomplished by comparing the activity design data transmitted from the remote system with corresponding activity design stored at the athletic data display configuration device 601. It should be understood that other embodiments may be utilized by to determine whether activity design data transmitted from a user device corresponds to activity design data stored on a remote server or other computing device.

In some example embodiments, the remote system may be configured to retrieve activity design data for a user from a remote computing device and compare that information to the activity design data transmitted from a device associated with the user (e.g., mobile computing device, wearable monitor, etc.). As will be appreciated, the processing and comparison of user activity design data may occur at any number of computing devices without departing from the scope of the present disclosure. After a user's identity has been confirmed or verified, the financial transaction or payment may be fully processed and completed.

III. Record of Achievements

As discussed above, various implementations of the present disclosure may provide positive reinforcement to an athlete. For example, a user can employ various embodiments of the invention to set goals for himself or herself, and then track his or her progress toward attaining those goals and performing various physical activities. Similarly, a user may employ various embodiments of the invention to participate in activity challenges. Once an activity goal is completed or the challenge is won, however, these achievements may be forgotten and thus not provide the user with any further positive reinforcement.

Accordingly, some implementations of the invention may provide a feature for memorializing a user's various athletic achievements. For example, with some embodiments of the invention, the athletic data display configuration module 605 may provide a user interface (e.g., interface 901) for displaying athletic achievements or milestones recorded for a user.

For example, if a user sets and then subsequently meets a goal, the achievement of this goal will be recorded by the athletic data display configuration module 605. In response, the athletic data display configuration module 605 will display an icon, such as a representation of a medal, graphically commemorating that achievement. Similarly, if the user wins a challenge, that achievement may be recorded by the athletic data display configuration module 605. In response, the athletic data display configuration module 605 may display an icon, such as a representation of a trophy, graphically commemorating that achievement. For example, FIG. 15 illustrates example awards that may be presented to a user via user interface. As will be discussed in more detail below, the user may have an option of physically printing a copy of the received award using a 3D printer.

Figure 16A:
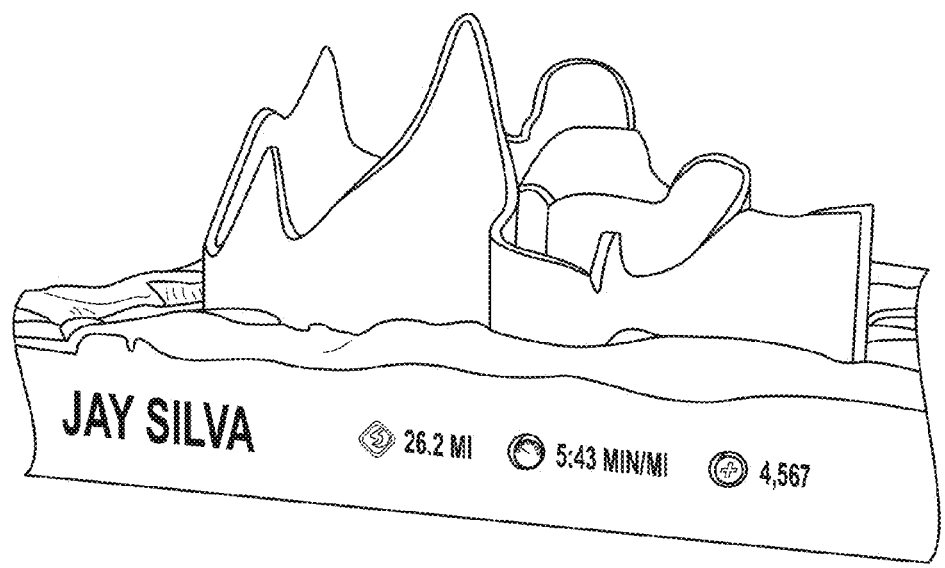
FIG. 16A shows an example display of a portion of an activity interface displaying athletic activity data in accordance with example embodiments.

Still further, a user may participate in an event (e.g., a race, a marathon) wherein athletic activity data corresponding to the user's athletic performance is collected and recorded in accordance with one or more implementations of the present disclosure. For example, if a user runs in a race, completes the race, or places in the race, then the athletic data display configuration module 605 may record that achievement. In response, the athletic data display configuration module 605 may display an icon, such as a representation of a racing bib, graphically commemorating that achievement. The athletic data display configuration module 605 may employ any desired technique to record the user's participation in the race. For example, the race sponsor may physically monitor the user's participation, and subsequently update the athletic data storage 607 directly. In some aspects of the present disclosure, the user may be provided with a graphic representation of the athletic activity data collected during an athletic event (e.g., a race). For example, as illustrated in FIG. 16 A, the system may display, via a user interface, a 3D graphical representation of user athletic activity data during the period in which the user participated in the event. As shown in this example, the graphical illustration of the user's athletic activity data may be color-coded to indicate various performance metrics, such as the varying rates at which the user exerted or expended energy (e.g., activity points per minute). Additionally or alternatively, the shape of the graphical representation may be used to indicate specific performance metrics, such as a total number of activity points achieved. For example, the higher portions of the graphical image illustrated in FIG. 16 A may represent athletic activity data corresponding to a time period in which the user earned the most activity points, while the lower portions of the graphical image may represent (or indicate) athletic activity data corresponding to a time period in which the user earned the least amount of activity points.

Of course, still more sophisticated techniques can be used to have the athletic data display configuration module 605 record the user's achievement. For example, the race sponsor or a third party may provide the user with an electronic recording device that records the user's progress through the race. The user can then download the data from the electronic recording device to the athletic data storage 607 or to the athletic data display configuration module 605. With some implementations of the invention, a wearable monitoring device including a sensor, such as sensor 128, may even be used to record the user's progress through the race, and to subsequently download the data from the electronic recording device to the athletic data storage 607 or to the athletic data display configuration module 605.

Still further, a user may have still other milestones associated with his or her athletic performance. For example, a user may run achieve a relatively large total distance, such as 100 kilometers, 100 miles, 250 kilometers, 250 miles, etc., run at a particularly fast speed, such as a mile in less than five minutes, or run for a relatively large total duration, such as 1000 hours. In response, the athletic data display configuration module 605 may record that milestone achievement, and then display an icon, such as a representation of an award ribbon, graphically commemorating that achievement.

In this manner, various implementations of the invention can memorialize a user's past achievements to provide the user with positive feedback to inspire future athletic performance. Of course, some implementations of the invention may memorialize alternate or additional achievements.

IV. 3D Printing of Consumer Products, Packaging, and Accessories

Figure 13:
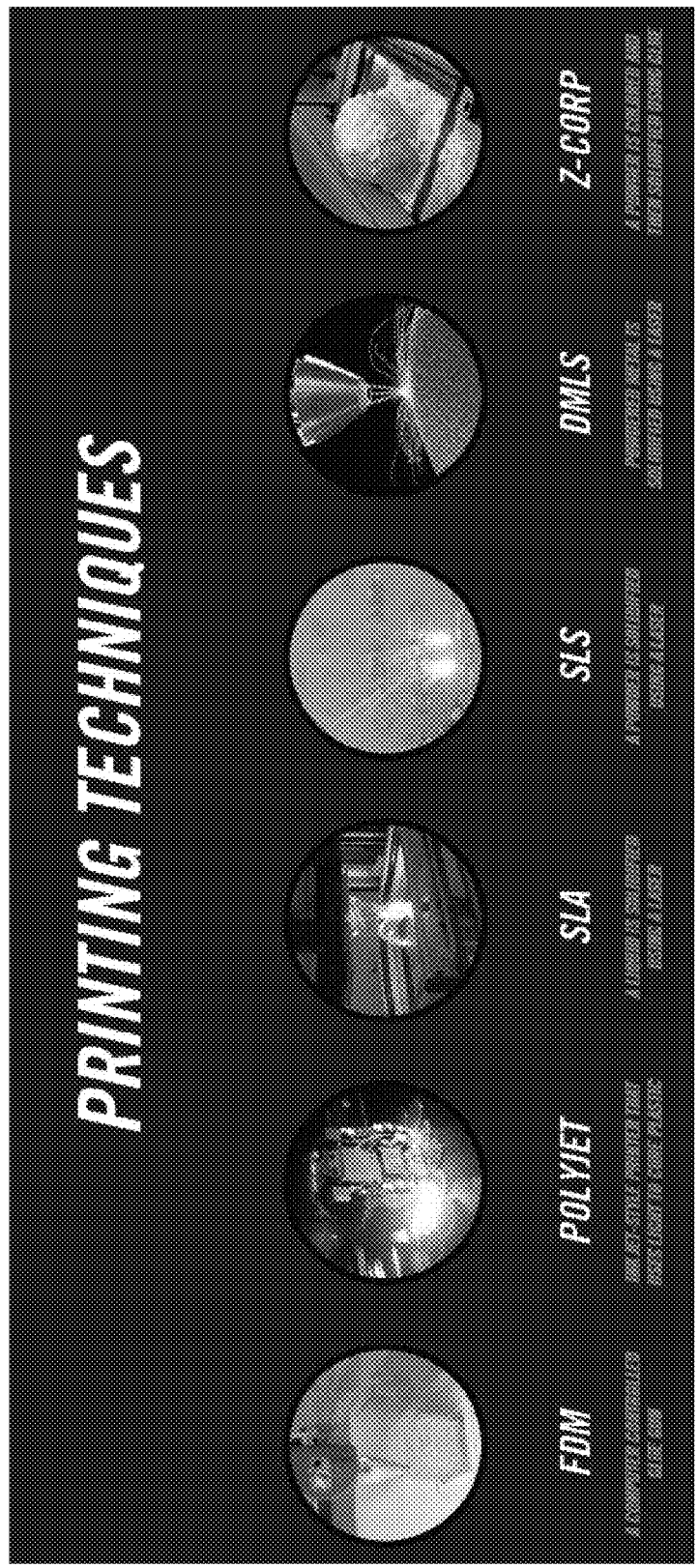
FIG. 13 shows an example display of a selection interface presented by a display screen of a computer device in accordance with example embodiments.
Figure 14:
FIG. 14 shows an example display of a selection interface presented by a display screen of a computer device in accordance with example embodiments.

In other aspects of this invention, a user may have the option customizing a consumer product, packaging, or accessory in accordance with one or more aspects of a design depicting the user's athletic data or performance, as discussed above. Information relating to the customized product, packaging, or accessory may be communicated to a product manufacture. The customized products may be created by a suitable manufacturing device, such as a 3D ("three-dimensional") printer. Referring to FIG. 13, the system may present the user with an interface displaying a variety of printing techniques for creating the customized product, such as a computer-controlled glue gun, a polyjet (e.g., an ink jet-style printer that uses light to cure plastic), solidifying liquids using a laser, solidifying powder using a laser, solidifying powdered metals using a laser, or coloring and solidifying a powder using glue. The system may prompt the user to select a particular printing technique for printing their customized product. Additional information associated with each of the various techniques, such as cost information and time to manufacture, may also be provided to the user via the interface illustrated in FIG. 13. Additionally or alternatively, as shown in FIG. 14, the user may be provided within an interface depicting the various materials that may be used to create the customized product, such as plastic, flexible plastic, transparent plastic, full color sandstone, ceramic, metals, and other suitable materials.

Figure 16B:
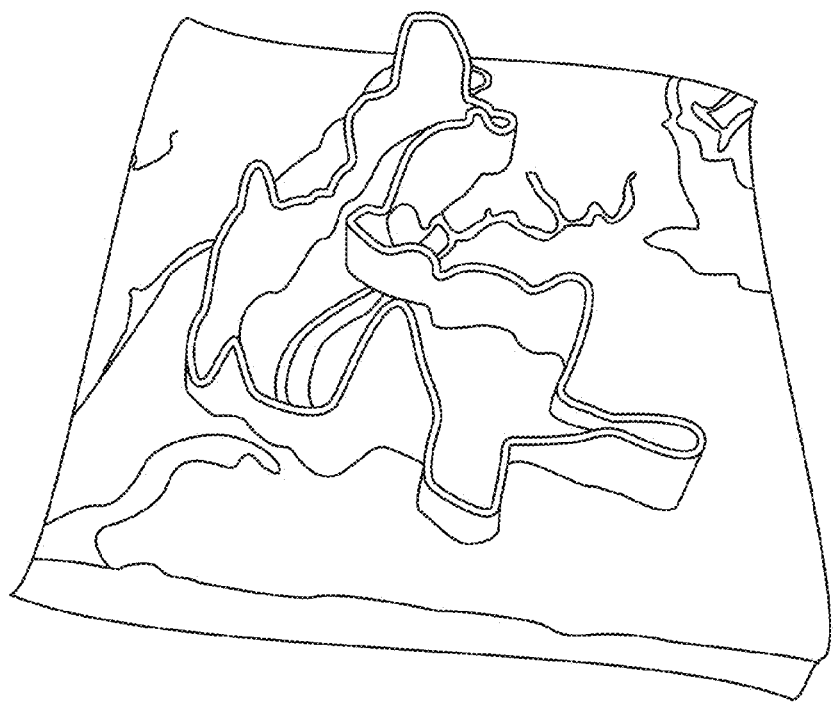
FIG. 16B shows an illustration of an example activity reward in accordance with example embodiments.

As discussed above, in some aspects of the present disclosure, a user may receive a reward or milestone upon reaching a certain point in a workout plan, or other athletic achievement. Much like the consumer products described above, rewards may be customized in accordance with one or more aspects of a design depicting the user's athletic data or performance, as discussed above with reference to FIG. 10B. For example, as illustrated in FIG. 15, a reward may represent a user achieving a particular athletic performance level (e.g., run level). As another example, the reward may represent a unique medal or medallion for participating in an athletic event. In this example, the reward may be configured to depict the user's athletic performance during an athletic event. As will be appreciated, the rewards described above may be created by a suitable manufacturing device, such as a 3D printer. In some aspects of the present disclosure, a user may create a physical representation of athletic activity data collected during an athletic activity event (e.g., a race) in order to commemorate that achievement. For example, FIG. 16B illustrates an exemplary reward that may be presented to and/or created by a user after competing in an athletic event. In this example, FIG. 16B illustrates a 3D reward representing the graphical representation of a user's athletic activity data shown in FIG. 16A. As will be appreciated, the rewards described above may be created by a suitable manufacturing device, such as a 3D printer.

Further aspects relate to creating consumer products, accessories, or packaging that may display a design representing athletic activity data the user and/or one or more users within a community. In some aspects of this invention, a user may have the option of adding a design depicting the user's athletic data or performance to the packaging for a custom manufactured product, such as any of the custom products described herein. For example, the packaging for a custom manufactured article of footwear (e.g., a shoe box) may have a design etched into the packaging itself.

CONCLUSION

While the invention has been described with respect to specific examples including presently preferred modes of carrying out the invention, those skilled in the art will appreciate that there are numerous variations and permutations of the above described systems and methods. For example, various aspects of the invention may be used in different combinations and various different sub-combinations of aspects of the invention may be used, together, in a single system or method without departing from the invention. In one example, software and applications described herein may be embodied as computer readable instructions stored in computer readable media. Also, various elements, components, and/or steps described above may be changed, changed in order, omitted, and/or additional elements, components, and/or steps may be added without departing from this invention. Thus, the invention should be construed broadly.

We claim:

1. A method comprising:
   obtaining, by a first computing device, a first set of athletic activity data relating to athletic activity performed by a first user for a plurality of time periods;
   determining performance metrics for one or more of the plurality of time periods;
   determining, based at least in part on the performance metrics, a color value for each of the one or more of the plurality or time periods;
   generating, based on the determined color values, a first activity design; and
   authenticating, by the first computing device and based on the first activity design, a payment transaction of the first user.

2. The method of claim 1, wherein the color value comprises an RGB color value.

3. The method of claim 1, further comprising:
   receiving user input selection identifying the performance metrics.

4. The method of claim 1, further comprising:
   receiving user input selection identifying a duration of the plurality of time periods.

5. The method of claim 1, wherein authenticating the payment transaction further comprises:
   receiving, from a second computing device, a second activity design;

comparing the first activity design to the second activity design; and in response to determining that the first activity design corresponds to the second activity design, authenticating the payment transaction.

6. The method of claim 1, wherein authenticating the payment transaction further comprises:

receiving, from a second computing device, biometric information for the first user; and authenticating, based in part on the received biometric information, the payment transaction.

7. The method of claim 1, further comprising:

encrypting the first activity design; and transmitting the first activity design to a remote device.

8. The method of claim 1, further comprising:

transmitting, to a remote device, the first activity design to activate a display of advertisements tailored to the first user.

9. The method of claim 1, further comprises:

receiving user input selection indicating a design pattern of the first activity design.

10. An apparatus comprising:

one or more processors; and memory operatively coupled to the one or more processors and storing computer readable instructions that, when executed cause the apparatus to:

obtain a first set of athletic activity data relating to athletic activity performed by a first user for a plurality of time periods;

determine performance metrics for one or more of the plurality of time periods;

determine, based at least in part on the performance metrics, a color value for each of the one or more of the plurality of time periods;

generate, based on the determined color values, a first activity design; and authenticate, based on the first activity design, a payment transaction of the first user.

11. The apparatus of claim 10, wherein the computer readable instructions, when executed, further cause the apparatus to:

receive user input selection identifying the performance metrics.

12. The apparatus of claim 10, wherein the computer readable instructions, when executed, further cause the apparatus to:

receive user input selection identifying a duration of the plurality of time periods.

13. The apparatus of claim 10, wherein the computer readable instructions, when executed, further cause the apparatus to authenticate the payment transaction by:

receiving, from a first computing device, a second activity design;

comparing the first activity design to the second activity design; and in response to determining that the first activity design corresponds to the second activity design, authenticating the payment transaction.

14. The apparatus of claim 10, wherein the computer readable instructions, when executed, further cause the apparatus to authenticate the payment transaction by:

receiving, from a first computing device, biometric information for the first user; and authenticating, based in part on the received biometric information, the payment transaction.

15. The apparatus of claim 10, wherein the computer readable instructions, when executed, further cause the apparatus to:

transmit, to a remote device, the first activity design to activate a display of advertisements tailored to the first user.

16. The apparatus of claim 10, wherein the computer readable instructions, when executed, further cause the apparatus to:

encrypt the first activity design; and transmit the first activity design to a remote device.

17. The apparatus of claim 10, wherein the color value comprises an RGB color value.

18. The apparatus of claim 10, wherein the computer readable instructions, when executed, further cause the apparatus to:

receive user input selection indicating a design pattern of the first activity design.

19. A non-transitory computer readable medium storing executable instructions that, when executed, cause an apparatus at least to perform:

obtaining a first set of athletic activity data relating to athletic activity performed by a first user for a plurality of time periods;

determining performance metrics for one or more of the plurality of time periods;

determining, based at least in part on the performance metrics, a color value for each of the one or more of the plurality or time periods;

generating, based on the determined color values, a first activity design; and authenticating, based on the first activity design, a payment transaction of the first user.

20. The non-transitory computer readable medium of claim 19, wherein the executable instructions, when executed, cause the apparatus to perform:

receiving, from a first computing device, a second activity design;

comparing the first activity design to the second activity design; and in response to determining that the first activity design corresponds to the second activity design, authenticating the payment transaction.

21. The non-transitory computer readable medium of claim 19, wherein the executable instructions, when executed, cause the apparatus to perform:

receiving, from a first computing device, biometric information for the first user; and authenticating, based in part on the received biometric information, the payment transaction.

22. The non-transitory computer readable medium of claim 19, wherein the executable instructions, when executed, cause the apparatus to perform:

transmit, to a remote device, the first activity design to activate a display of advertisements tailored to the first user.

23. The non-transitory computer readable medium of claim 19, wherein the executable instructions, when executed, cause the apparatus to perform:

receiving user input selection identifying the performance metric.

24. The non-transitory computer readable medium of claim 19, wherein the executable instructions, when executed, cause the apparatus to perform:

receiving user input selection identifying a duration of the plurality of time periods.

25. The non-transitory computer readable medium of claim 19, wherein the executable instructions, when executed, cause the apparatus to perform:
- receiving, from a first computing device, a second activity design;
- comparing the first activity design to the second activity design; and
- in response to determining that the first activity design corresponds to the second activity design, authenticating the payment transaction.

26. The non-transitory computer readable medium of claim 19, wherein the executable instructions, when executed, cause the apparatus to perform:
- encrypting the first activity design; and
- transmitting the first activity design to a remote device.

27. The non-transitory computer readable medium of claim 19, wherein the executable instructions, when executed, cause the apparatus to perform:
- receiving user input selection indicating a design pattern of the first activity design.

\* \* \* \* \*